US012458764B2

(12) United States Patent
Connolly et al.

(10) Patent No.: US 12,458,764 B2

(45) Date of Patent: Nov. 4, 2025

(54) VIBRATING APERTURE PLATE NEBULIZER

(71) Applicant: STAMFORD DEVICES LIMITED, Galway (IE)

(72) Inventors: Diarmuid Connolly, Galway (IE); Colm Carmody, Galway (IE); Finbarr Maguire, County Clare (IE); Aidan Duffy, Galway (IE); Michael Timothy, County Galway (IE)

(73) Assignee: STAMFORD DEVICES LIMITED, Galway (IE)

(*) Notice: Subject to any disclaimer, the term of this patent is extended or adjusted under 35 U.S.C. 154(b) by 428 days.

(21) Appl. No.: 17/907,203

(22) PCT Filed: Mar. 22, 2021

(86) PCT No.: PCT/EP2021/057307

§ 371 (c)(1),
(2) Date: Sep. 23, 2022

(87) PCT Pub. No.: WO2021/191163

PCT Pub. Date: Sep. 30, 2021

(65) Prior Publication Data

US 2023/0104205 A1 Apr. 6, 2023

(30) Foreign Application Priority Data

Mar. 24, 2020 (EP) .................................... 20165404
Mar. 24, 2020 (EP) .................................... 20165407
(Continued)

(51) Int. Cl.
*A61M 11/00* (2006.01)
*B05B 17/00* (2006.01)

(52) U.S. Cl.
CPC ....... *A61M 11/005* (2013.01); *B05B 17/0646* (2013.01); *A61M 2207/10* (2013.01)

(58) Field of Classification Search
CPC ............ A61M 15/0085; A61M 11/001; A61M 11/005; A61M 2207/10; B05B 17/04;
(Continued)

(56) References Cited

U.S. PATENT DOCUMENTS 6,539,937 B1 * 4/2003 Haveri .................. B06B 1/0253
128/200.14
9,289,792 B2 * 3/2016 Hogan ................. A61M 11/001
(Continued)

FOREIGN PATENT DOCUMENTS

CN 107530717 * 1/2018 ............... B05B 1/02
EP 1005916 A1 6/2000
(Continued)

OTHER PUBLICATIONS

International Search Report in PCT/EP2021/057307, mailed Jun. 24, 2021.
EN ISO 4287:1998/A1:2009.

*Primary Examiner* — Christopher R Dandridge
(74) *Attorney, Agent, or Firm* — Bookoff McAndrews, PLLC

(57) ABSTRACT

A nebulizer has an aerosol generator, a reservoir, and an aerosol outlet. A piezoelectric vibration generator is on a downstream side of a support washer, and power to the piezo is provided by a spring contact assembly. The assembly has upstanding electrical terminals for contact with electrical supply conductors. There are spring terminals extending around a rim of the spring contact assembly to engage an exposed underside of the washer, and a resilient ridge extending in the upstream direction to engage the underside of the piezo, which itself is on the downstream side of the washer.

25 Claims, 27 Drawing Sheets

(30) Foreign Application Priority Data

Mar. 24, 2020 (EP) .................................... 20165409
Mar. 24, 2020 (EP) .................................... 20165410

(58) Field of Classification Search
CPC ............ B05B 17/0646; B05B 17/0607; B05B 17/0615; B05B 17/063; B05B 17/0638
USPC ...................................................... 239/102.2
See application file for complete search history.

(56) References Cited

U.S. PATENT DOCUMENTS

| | | | | |
|---|---|---|---|---|
| 2003/0019493 | A1* | 1/2003 | Narayan | A61M 15/0065 128/200.14 |
| 2003/0218077 | A1* | 11/2003 | Boticki | B05B 17/0676 239/102.1 |
| 2011/0230820 | A1* | 9/2011 | Lillis | A61M 13/00 604/24 |
| 2012/0091224 | A1* | 4/2012 | Yu | B05B 17/0646 239/102.2 |
| 2015/0034075 | A1 | 2/2015 | Gallem et al. | |
| 2015/0375252 | A1 | 12/2015 | Lee et al. | |
| 2018/0178226 | A1* | 6/2018 | Morgan | B25B 27/14 |
| 2018/0193869 | A1 | 7/2018 | Biette | |

FOREIGN PATENT DOCUMENTS

| | | | |
|---|---|---|---|
| EP | 3308865 | A1 | 4/2018 |
| EP | 3560604 | A1 | 10/2019 |
| WO | 2012046220 | A1 | 4/2012 |
| WO | 2012092163 | A1 | 7/2012 |
| WO | 2014133273 | A1 | 2/2013 |
| WO | 2013186031 | A2 | 12/2013 |
| WO | 2016151029 | A1 | 9/2016 |
| WO | 2018128629 | A1 | 7/2018 |
| WO | 2019115221 | A1 | 6/2019 |
| WO | 2019196876 | A1 | 10/2019 |
| WO | 2019214281 | A1 | 11/2019 |

* cited by examiner

VIBRATING APERTURE PLATE NEBULIZER

INTRODUCTION

The invention relates to nebulizers of the type having a vibrating aperture plate aerosol generator.

Our prior specification WO2012046220A describes an aerosol generator with a funnel-shaped housing top part forming a reservoir, inclined to the axis of a tubular lower part. An aperture plate ("AP") is attached to a washer-shaped support on which there is an annular piezoelectric vibration generator. Power is provided via pins to the top of the piezo directly and via the washer to the bottom of the piezo. Such a nebulizer works very effectively.

However, vibrating aperture plate nebulisers naturally tend to ingest air through the centre of the aperture plate when nebulising. These bubbles have a size in the micrometre range and have the potential to migrate to the walls of the nebuliser throat over the aperture plate. Here they may stagnate, coalesce and form a larger air bubble. These larger air bubbles can reduce or interrupt nebulization. Sometimes it helps to tap the nebuliser to release the air bubble and recommence nebulisation.

Our prior published patent specification WO2016151029A describes an approach to bubble prevention which involves providing physical features in the interior reservoir surface, to physically prevent bubbles from forming to be large.

The present invention is directed towards achieving improvements in efficiency and consistency of conversion of the liquid into aerosol and/or more efficient robotic manufacture of the nebulizer.

SUMMARY

The invention is set out in claim 1 and its dependent claims.

We describe nebulizers comprising: a housing, a liquid supply reservoir, an aerosol outlet, and an aerosol generator comprising:

- a vibratable aperture plate,
- an annular support supporting the aperture plate,
- a vibration generator attached to the annular support,
- a power conductor for transferring power to the vibration generator,
- a downstream resilient seal mounted on a side of the aperture plate opposed to the liquid supply reservoir, and
- an upstream resilient seal mounted between the annular support and the housing reservoir.

Preferably, in some examples, the power conductor comprises at least one first spring contact engaging an underside of the support or vibration generator on the downstream side, and a second spring contact engaging the underside of the vibration generator or support, said first and second spring contacts provide power delivery to the vibration generator. These spring contacts preferably apply spring forces arising from being cantilevered and/or being bent between an anchor and a free end.

In some examples, the vibration generator is mounted to a downstream side of the support.

In some examples, the second spring contact directly contacts the vibration generator. In some examples, the support extends further radially than the vibration generator, and the first spring contact engages a support surface laterally of the vibration generator. In some examples, at least one of said spring contacts is in the form of a resilient ridge which is arc-shaped in axial, longitudinal, view. The resilient ridge may extend at least partly around the aperture plate. In some examples, the resilient ridge extends in the upstream direction from a contact assembly base, and said base also supports a spring contact which extends radially outwardly and bends radially inwardly to engage a support or vibration generator surface. Preferably, the bend provides the resilience for said spring contact. In some examples, said spring contact with a bend engages the support radially outwardly of the vibration generator. In some examples, the spring contacts are mounted to a contact assembly which is mounted to the housing on a downstream side of the aperture plate.

In some examples, the power conductor comprises at least two conducting spring pins, on the upstream side of the aerosol generator. In some examples, a first spring pin engages an upstream-facing surface of the support and a second spring pin contacts an upstream-facing surface of the vibration generator, wherein said second spring pin extends through an aperture of the annular support without conductively contacting the support. Preferably, the first pin contacts the upstream surface of the support for conducting power to an opposed side of the piezo which is isolated from an area of contact between the second pin and the vibration generator.

In some examples, a first pin engages the annular support for transfer of power to an upstream side of the vibration generator, and a second pin engages a conductive clip having an upstream limb and a downstream limb joined by a web, the downstream limb engaging the downstream side of the vibration generator, and the web extending around the annular support outer edge.

In some examples, the aerosol generator is mounted to a retainer, and said retainer engages the housing. In some examples, the retainer comprises a retaining clip which extends in an upstream direction to engage the housing adjacent the aerosol generator. In some examples, the retainer comprises at least two ramps which are facing radially outwardly for guiding insertion of the retainer into the housing, In some examples, the reservoir and the aerosol outlet are inter-connected by an ultrasonic weld.

In some examples, at least some of the surface of the reservoir has a hydrophilic coating.

In some examples, the vibration generator comprises a piezoelectric vibration generator having an internal diameter in excess of 6 mm and preferably in excess of 7 mm. In some examples, the upstream seal has an internal diameter in excess of 7 mm. In some examples, the upstream resilient seal is in the form of a gasket having a body and a downstream-extending rim forming an opening, the body extending radially from said rim in a substantially annular shape, wherein the gasket comprises at least one upwardly-directed ridge for engagement with a housing surface, and wherein the gasket body overlies at least part of the annular support. In some examples, there are two or more upwardly-directed ridges, and wherein at least one of said ridges is circular in plan. In some examples, the ridges have a height in the range of 0.1 mm and 0.5 mm, and the downstream-extending rim has a depth relative to the gasket body in the range of 0.5 mm and 1.1 mm.

In some examples, the upstream resilient seal is configured so that when under axial compression it forms an opening with an internal surface which is tapered inwardly in a flow direction to form a funnel shape at a throat over the aperture plate. In some examples, some of the opening internal surface is formed by a downstream ridge of the upstream resilient seal.

In some examples, the gasket body overlies at least part of the vibration generator, said vibration generator being mounted to an upstream surface of the support. In some examples, the retainer is snap-fitted within the aerosol outlet, with engagement between the retainer and the aerosol outlet being assisted by compression and axial reactive force of the downstream resilient seal and the upstream resilient seal. In some examples, the retainer comprises an annular seat for the downstream resilient seal; and wherein the support, the aperture plate, the vibration generator, and the upstream resilient seal are supported over said downstream resilient seal; and wherein the retainer forms an annular seat for the upstream resilient seal.

In some examples, the power conductor comprises a pair of conducing spring pins and one or both of said pins extends through an aperture in the gasket. In some examples, the gasket has a Shore hardness in the range of 30 to 60 Shore A. In some examples, the gasket comprises a plurality of downstream ridges. In some examples, the gasket extends in the radial direction to form a resilient seal between plastics housing parts and extends in the radial direction to completely overlie the support.

In some examples, the upstream resilient seal has a surface exposed to the reservoir to form at least part of a throat over the aperture plate, and has on at least some of said exposed surface a surface roughness average in the range of 1.6 μm to 3.2 μm.

In some examples, the upstream resilient seal has an internal surface which forms a continuation of an internal surface of the reservoir to form a throat over the aperture plate. In some examples, the throat is funnel-shaped.

In some examples, said throat has an area in the plane of the aperture plate of at least 18 $mm^2$, preferably at least 20 $mm^2$, and optionally at least 25 $mm^2$. In some examples, the throat has an area in the plane of the aperture plate of at least twice the active area of the aperture plate.

Additional Statements

We describe a nebulizer comprising:

- a housing,
- a liquid supply reservoir formed by the housing,
- an aerosol outlet in the housing,
- an aerosol generator mounted in the housing and comprising:
  - a vibratable aperture plate,
  - an annular support supporting the aperture plate,
  - a vibration generator attached to the annular support,
  - a power conductor for transferring power to the vibration generator,
  - a downstream annular resilient seal mounted between the housing and the annular support on a downstream side of the aperture plate opposed to the liquid supply reservoir, and
  - an upstream resilient seal mounted between the annular support and the housing reservoir, and having an opening forming part of a throat over the aperture plate.

Preferably, the upstream resilient seal is in the form of a gasket having a body and a downstream-extending rim adjacent the opening, the body extending radially from said rim in a substantially annular shape. Preferably, the gasket comprises at least one upwardly-directed ridge for engagement with a housing surface. Preferably, there are two or more upwardly-directed ridges. Preferably, at least one of said ridges is circular in plan, preferably concentric.

Preferably, the ridges have a height (relative to the gasket body) in the range of 0.1 mm and 0.5 mm, and the downstream-extending rim has a height (relative to the gasket body) in the range of 0.5 mm and 1.1 mm. Preferably, the gasket is configured so that when under axial compression the opening internal surface is tapered inwardly in a flow direction to form a funnel shape.

Preferably, some of the opening internal surface is formed by the downstream ridge. Preferably, the gasket body overlies at least part of the annular support.

Preferably, the gasket body overlies at least part of the vibration generator.

Preferably, the gasket overlies and is in contact with an upper surface of the vibration generator, said vibration generator being mounted to a top surface of the support.

Preferably, the housing comprises a retainer which is engageable with an aerosol outlet part of the housing, and the aerosol generator is supported by the retainer underneath the liquid supply chamber. Preferably, the retainer is snap-fitted within the aerosol outlet, with engagement between the retainer and the aerosol outlet being assisted by compression and axial reactive force of the upstream and downstream resilient seals.

Preferably, the retainer comprises an annular seat for the downstream resilient seal, and wherein the support, the aperture plate, the vibration generator, and the gasket are supported over said lower resilient seal. Preferably, the retainer forms an annular seat for the gasket.

Preferably, the retainer comprises circumferential and axially-directed tabs forming side walls of said gasket seat.

Preferably, the throat has an area in the plane of the AP of at least 18 $mm^2$, more preferably at least 20 $mm^2$, more preferably at least 25 $mm^2$, more preferably at least 30 $mm^2$.

In one preferred example, the throat has an area in the plane of the AP in the range of about 32 $mm^2$ to 40 $mm^2$.

Preferably, the throat has an area in the plane of the AP of at least twice the active area of the aperture plate.

Preferably, the gasket opening has a diameter when in the housing and compressed in excess of 5 mm, and preferably in excess of 5.5 mm, and more preferably in excess of 6.0 mm.

Preferably, the gasket opening has an axial dimension in excess of 2.0 mm. Preferably, the nebulizer comprises a pair of conducing spring pins for driving the vibration generator, and one or both of said pins extends through an aperture in the gasket.

Preferably, the gasket is of medical grade liquid silicone rubber supplied as two component compounds which are mixed together and injected into a hot mould to cure.

Preferably, the gasket has a Shore hardness in the range of 20 to 80 Shore A, more preferably in the range of 30 to 60 Shore A.

In one preferred example, the gasket comprises a plurality of downstream ridges.

In one preferred example, the vibration generator is mounted to an upstream surface of the support, and at least one downstream-extending ridge extends around an outer periphery the vibration generator.

In one preferred example, the gasket extends in the radial direction to form a resilient seal between plastics housing parts.

In one preferred example, the gasket extends in the radial direction to completely overlie the vibration generator.

In one preferred example, the gasket extends in the radial direction to completely overlie the support.

In one preferred example, the gasket extends in the radial direction to engage the housing at its outer edge.

In one preferred example, the gasket has on at least some of its exposed surface a surface roughness in the range of 1.6 μm to 3.2 μm.

In one preferred example, the gasket has on at least some of its exposed surface a hydrophilic coating. In one example, at least some of the surface of the reservoir has a hydrophilic coating.

In one example, the vibration generator comprises a piezoelectric vibration generator having an internal diameter in excess of 6 mm and preferably in excess of 7 mm.

In one example, the upstream seal has an internal diameter in excess of 7 mm.

In one example, the vibration generator is mounted to a downstream side of the support.

In one example, the support and the vibration generator are combined as a core assembly.

In one example, the power conductor comprises one or more spring contact.

The power conductor may comprise at least one first spring contact engaging an underside of the support or vibration generator on the downstream side, and a second spring contact engaging the underside of the vibration generator or support, said first and second spring contacts providing opposed electrical contacts for power delivery to the vibration generator.

The support may extend further radially than the vibration generator, and the first spring contact engages a support surface laterally of the vibration generator.

The second spring contact may directly contact the vibration generator.

At least one of said spring contacts may be in the form of a resilient ridge which is arc-shaped in axial (longitudinal) view.

The resilient ridge may extend at least partly around the aperture plate.

The resilient ridge may extend in the upstream direction from a contact assembly base, and said base also supports a spring contact which extends radially outwardly and bends radially inwardly to engage a support or vibration generator surface. The bend may provide the resilience for said spring contact. Said spring contact with a bend may engage the support radially outwardly of the vibration generator.

The spring contacts may be mounted to a contact assembly which is mounted to the housing on a downstream side of the aperture plate.

The power conductor may comprise at least two conducting spring pins, at least one engaging an upstream-facing surface of the support and at least one other pin contacting an upstream-facing surface of the vibration generator.

The vibration generator may be mounted to a downstream-facing surface of the support, and the pin contacting the vibration generator may extend through an aperture of the support without conductively contacting the support.

The retainer may comprise a retaining clip which extends in an upstream direction to engage the reservoir housing adjacent the aerosol generator.

The reservoir and the aerosol conduit may be interconnected by an ultrasonic weld.

We also describe a method of manufacturing a nebulizer of any described example, the method comprising mounting the aerosol generator to the retainer and moving robotically the retainer towards the housing reservoir until the retainer snap fits into position onto the housing, being retained by axial resilient reactive forces of the upstream and downstream seals.

DETAILED DESCRIPTION OF THE INVENTION

The invention will be more clearly understood from the following description of some embodiments thereof, given by way of example only with reference to the accompanying drawings in which.

Figure 5:
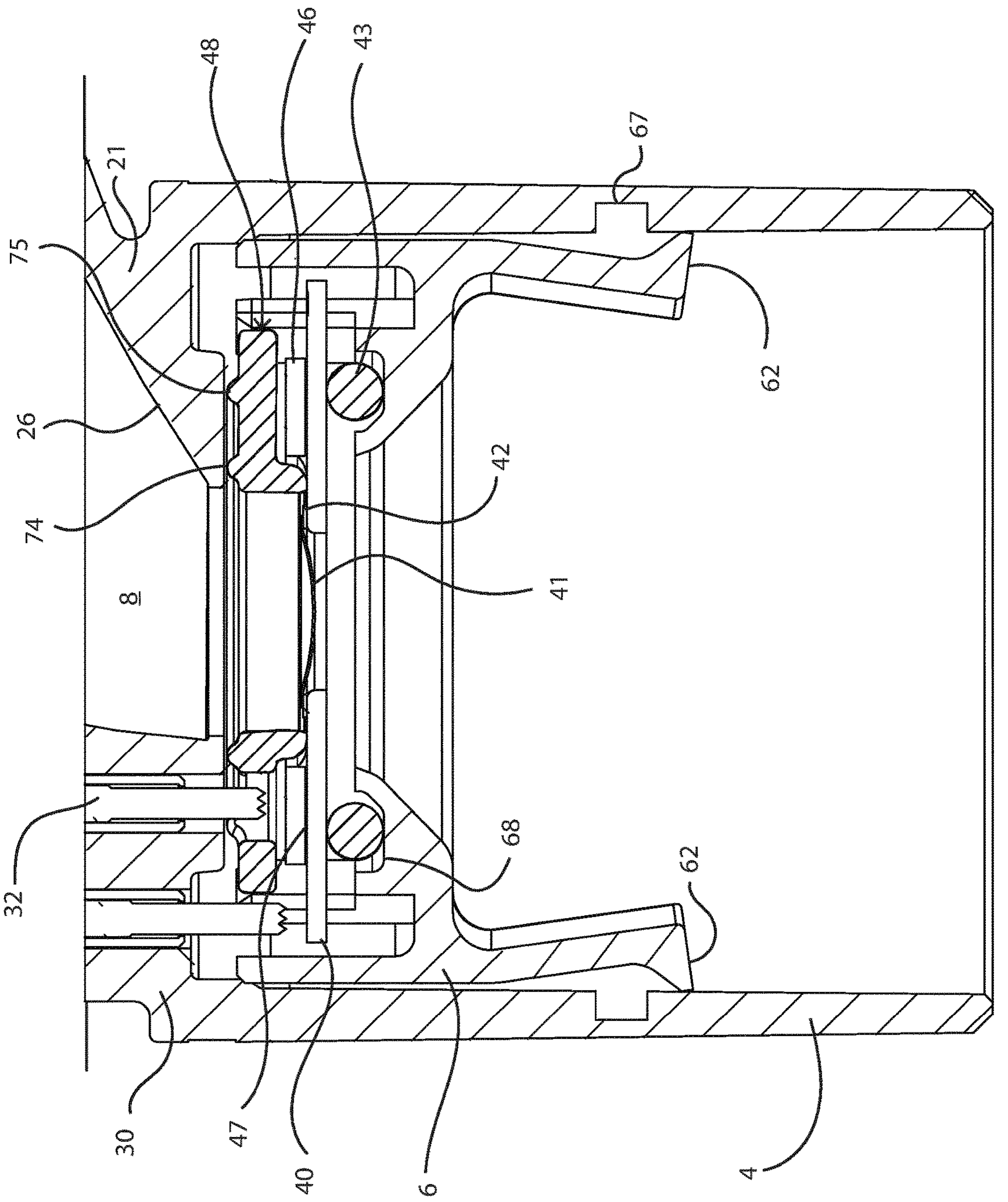
Figure 6:
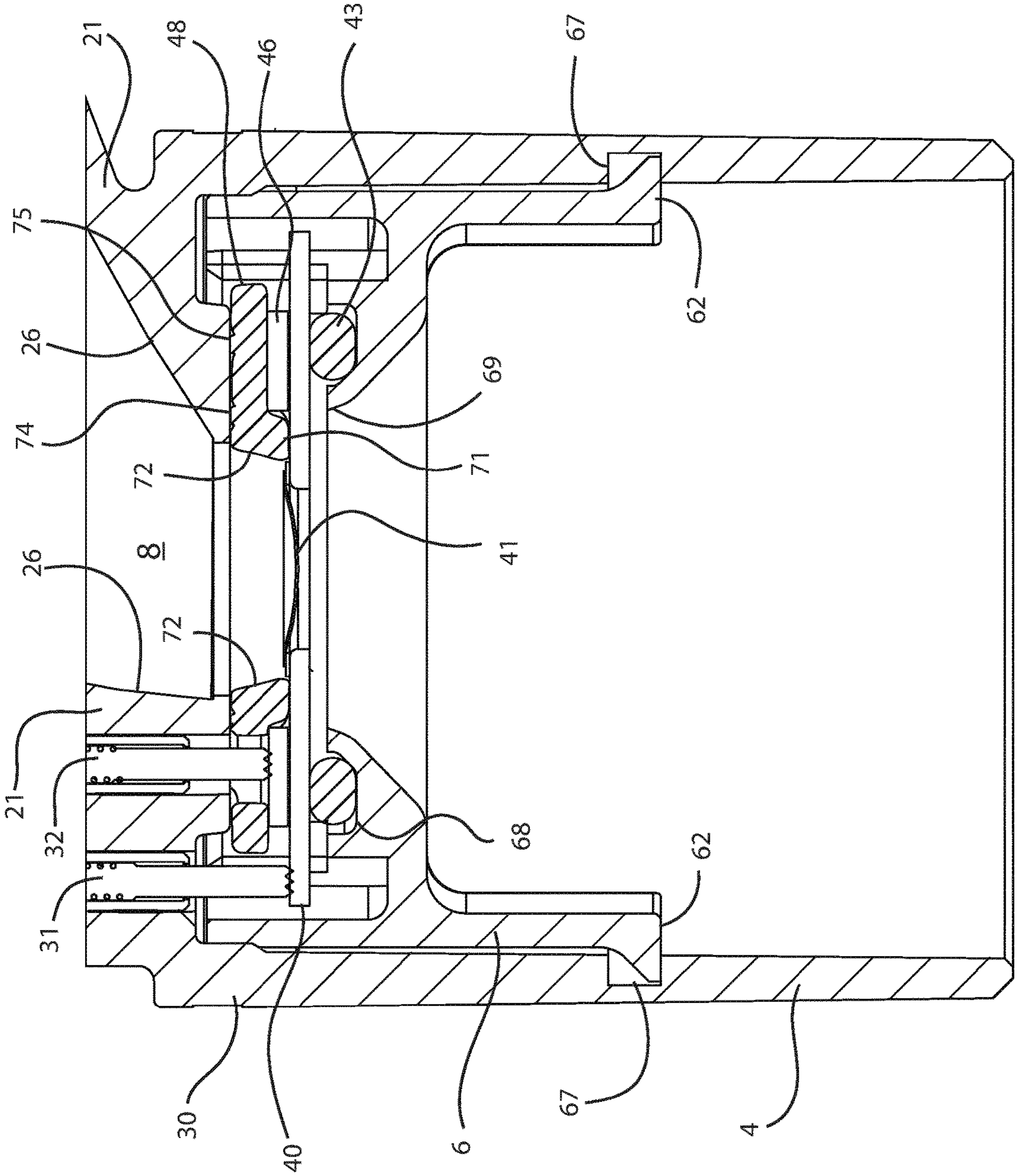
Figure 7:
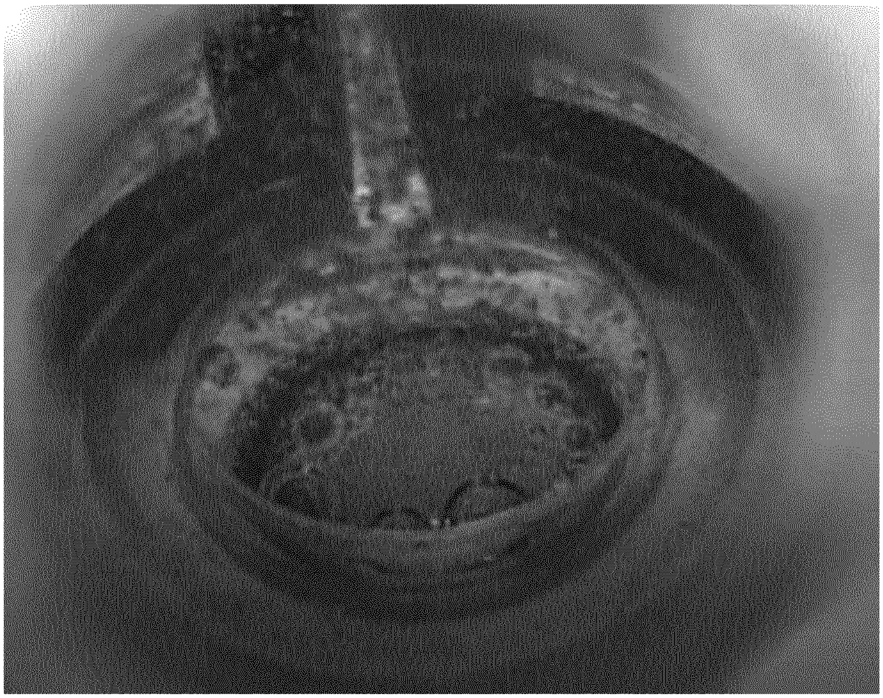
Figure 8:

(a) perspective view, (b) cross-sectional view through the gasket, showing an aperture for a conducting pin, (c) top plan view, and (d) bottom plan view;

FIG. 5 is a cross sectional view during assembly, before the conducting pins make contact; and FIG. 6 is a similar view to that of FIG. 5, in this case after the pins are contacting the piezoelectric vibration generator ("piezo") and the support washer, with the retainer snap-fitted into place;

FIG. 7 is an image showing bubble formation on the aperture plate, especially around the rim where it is attached by brazing to the support washer, and FIG. 8 is a pair of magnified images showing the surfaces of two gaskets, which are configured to minimize bubble retention and enlargement at the gasket surface.

Figure 9:
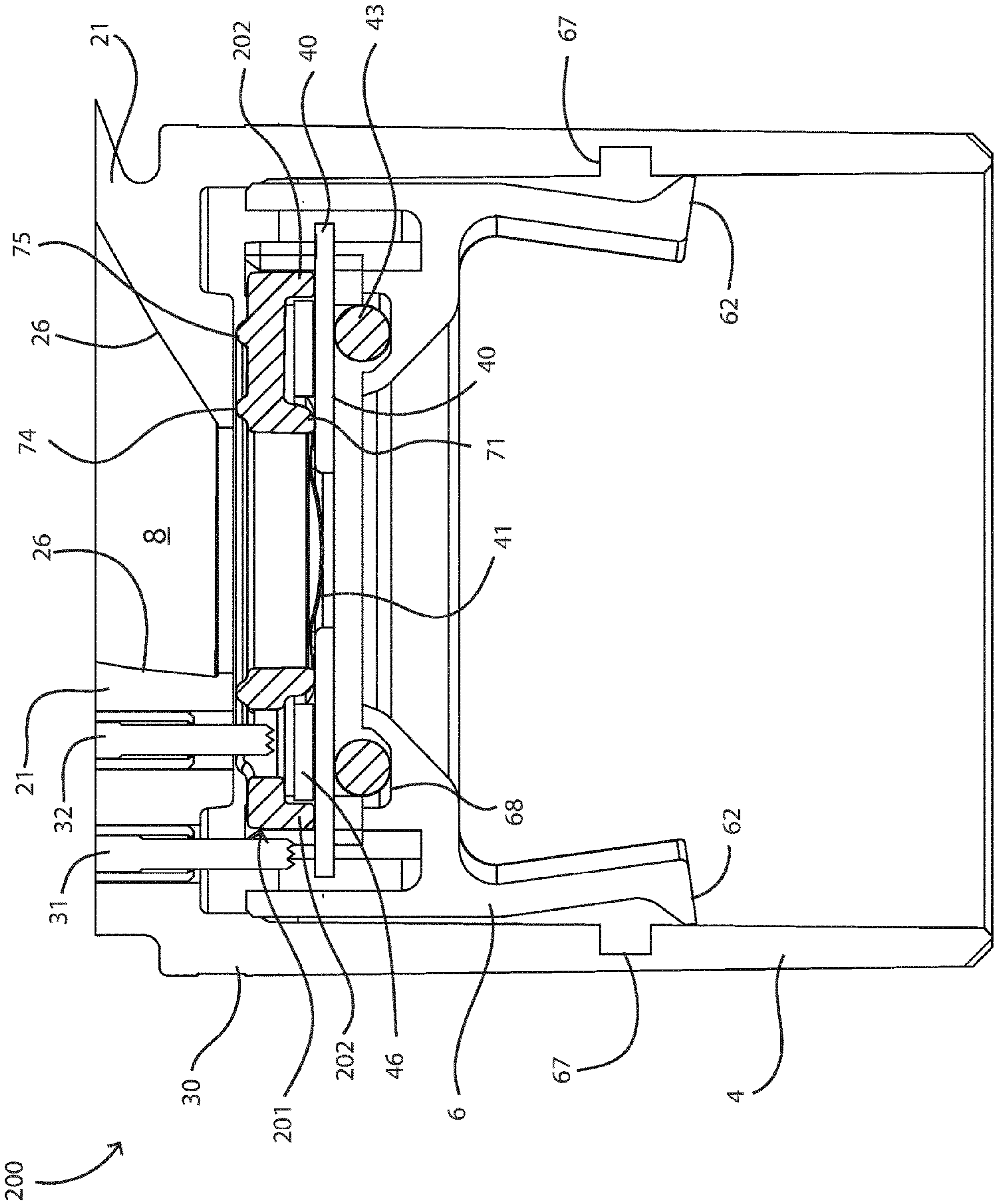
Figure 10:
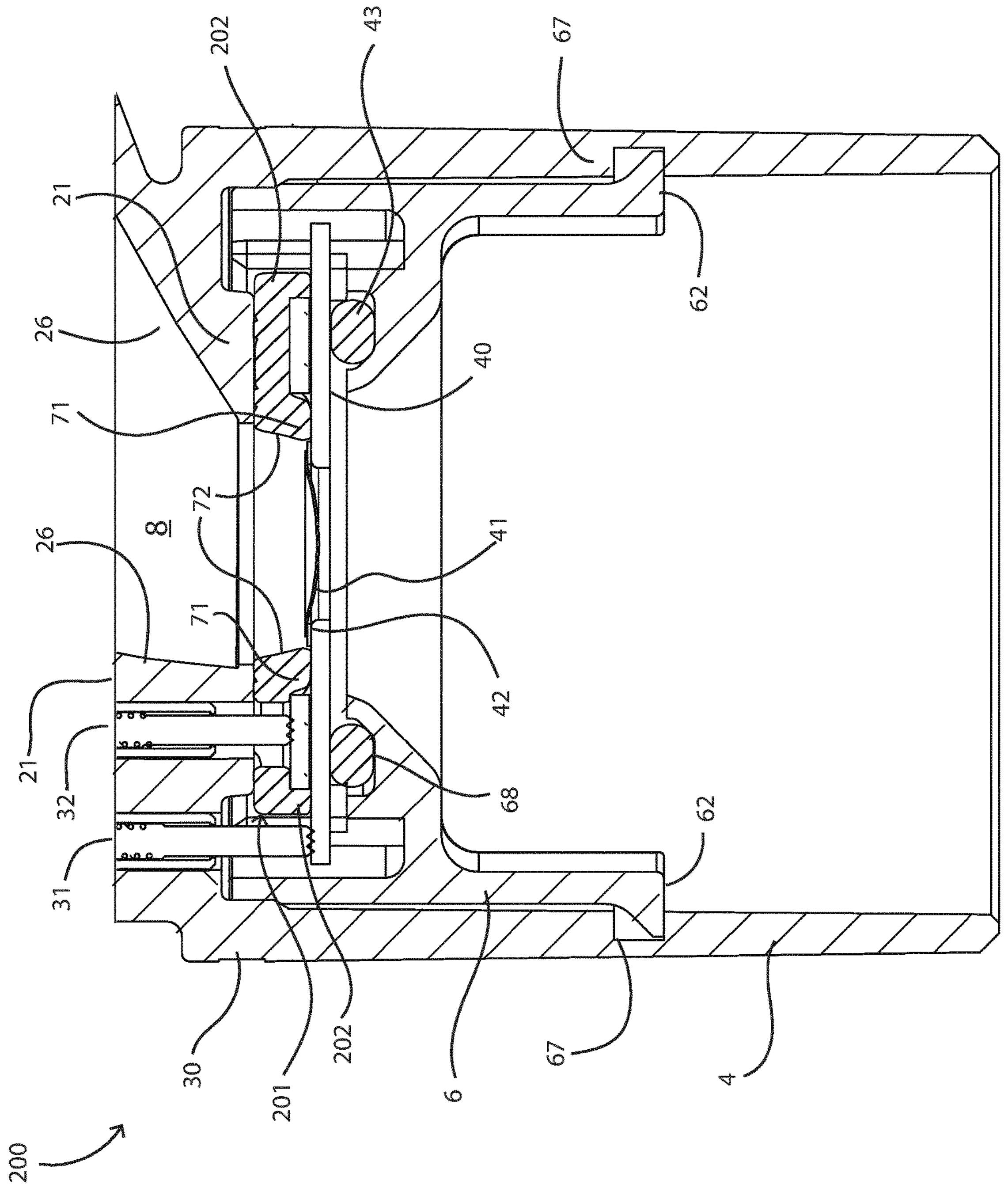
Figure 11:
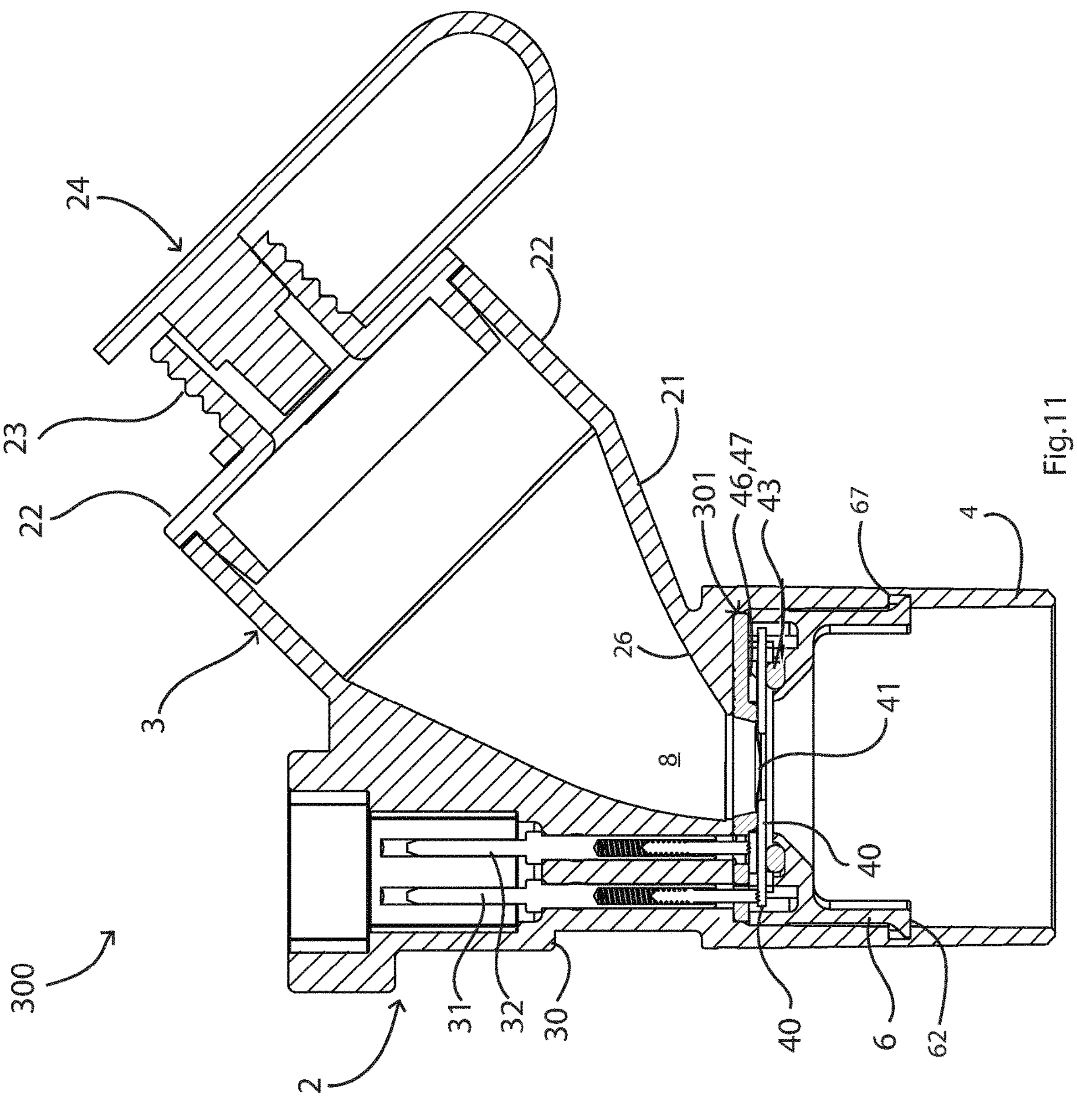
Figure 15:
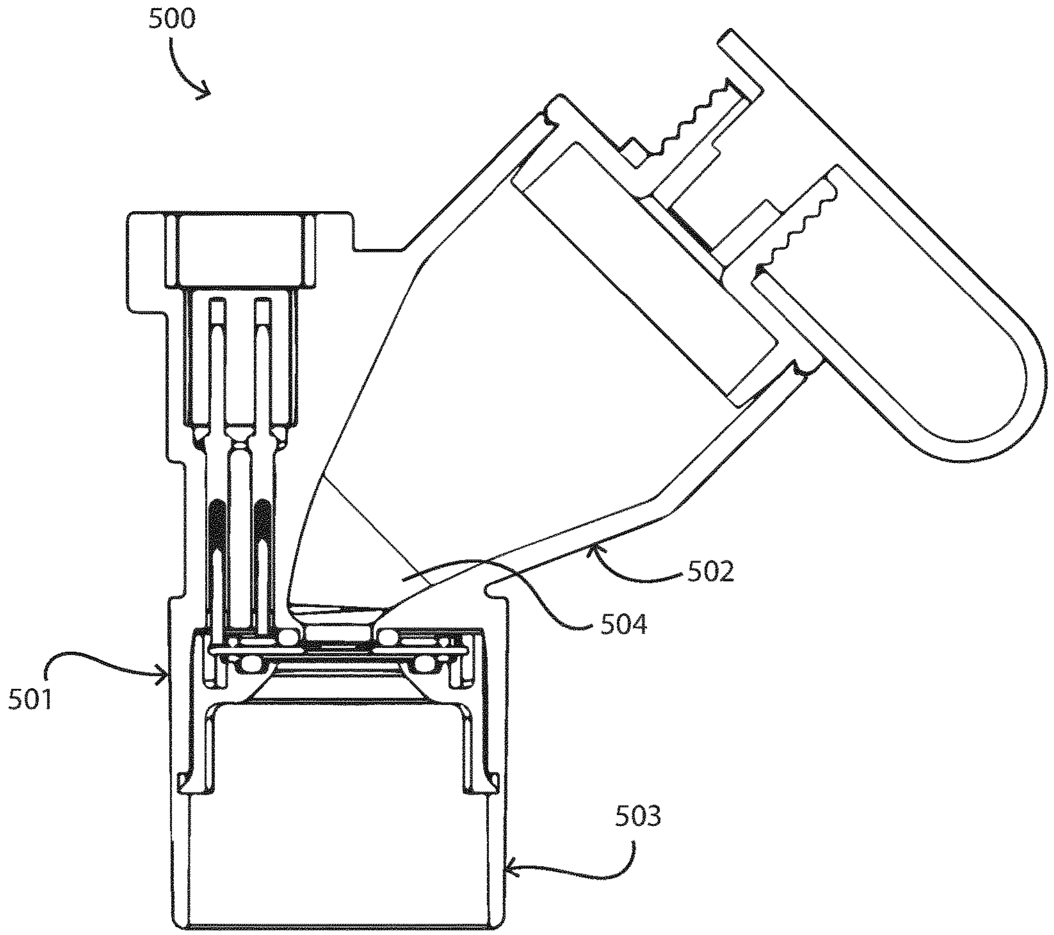
Figure 16:
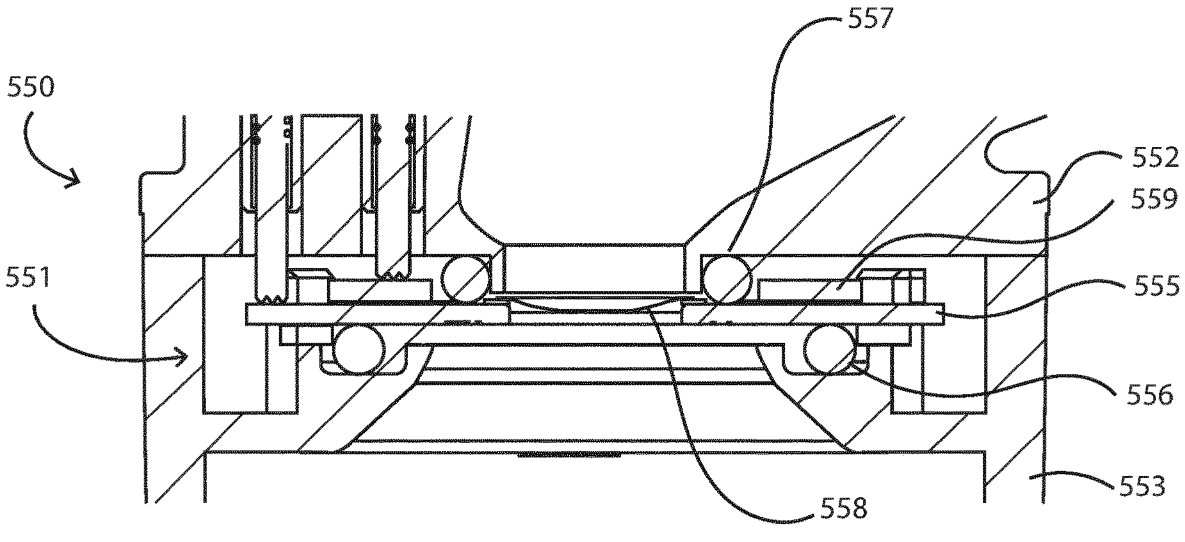
Figure 17:
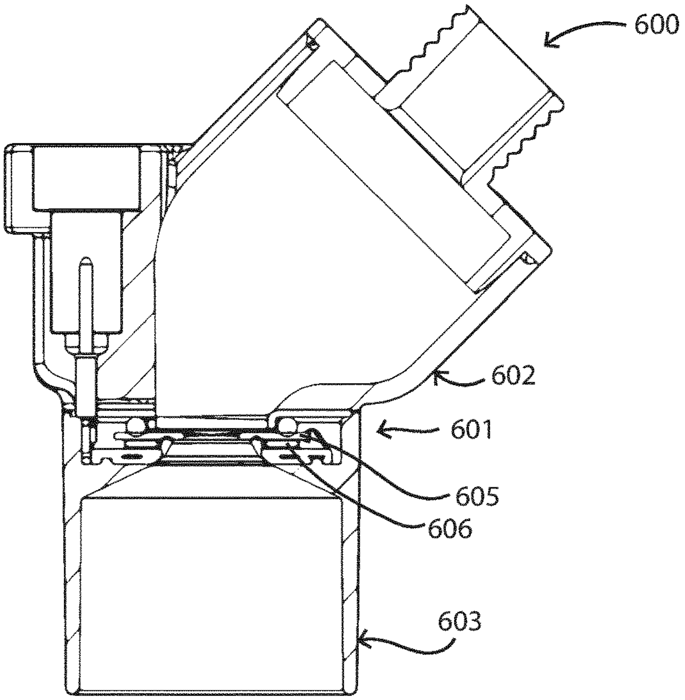
Figure 17:
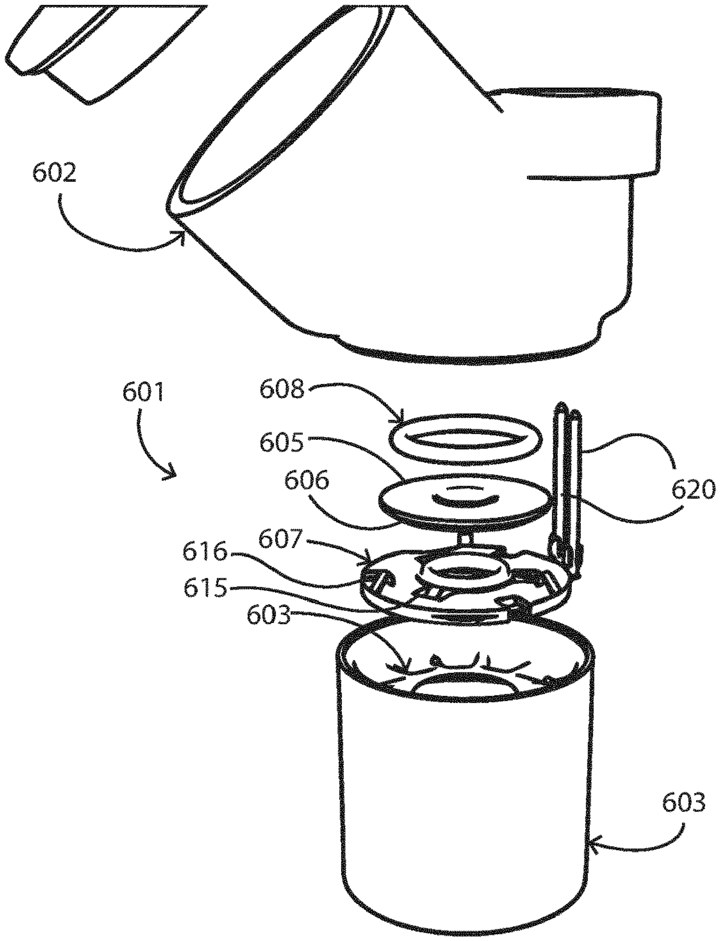
Figure 20:
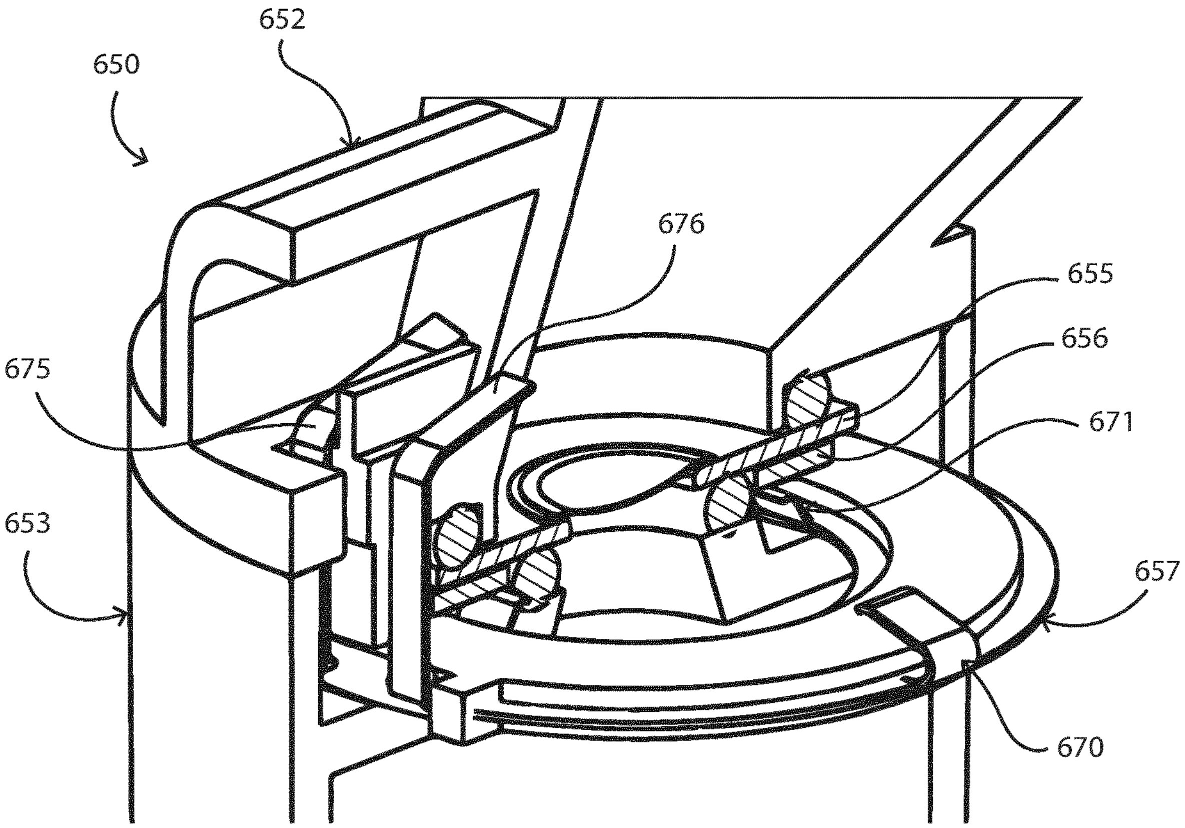
Figure 21A:
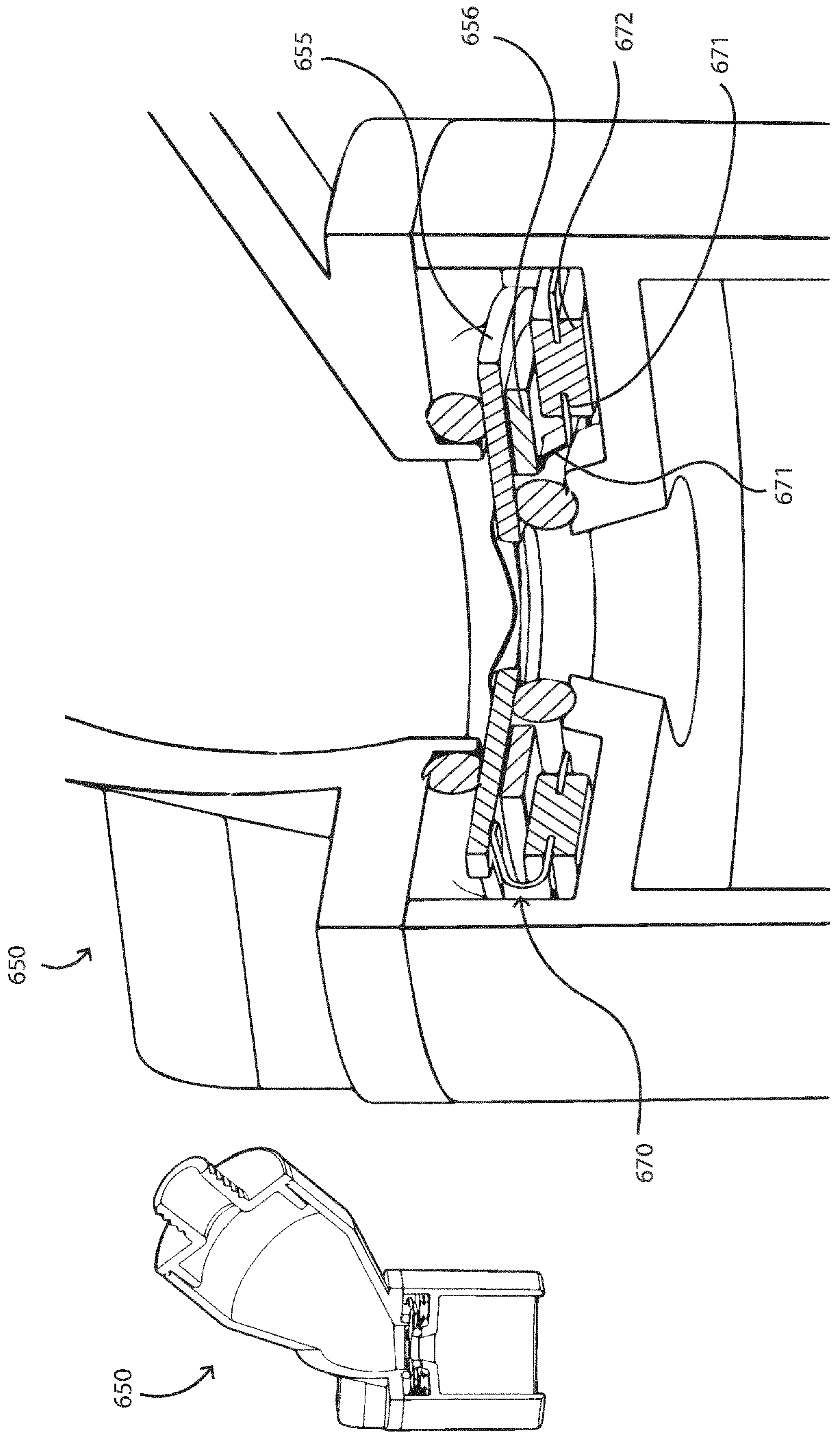
Figure 21B:
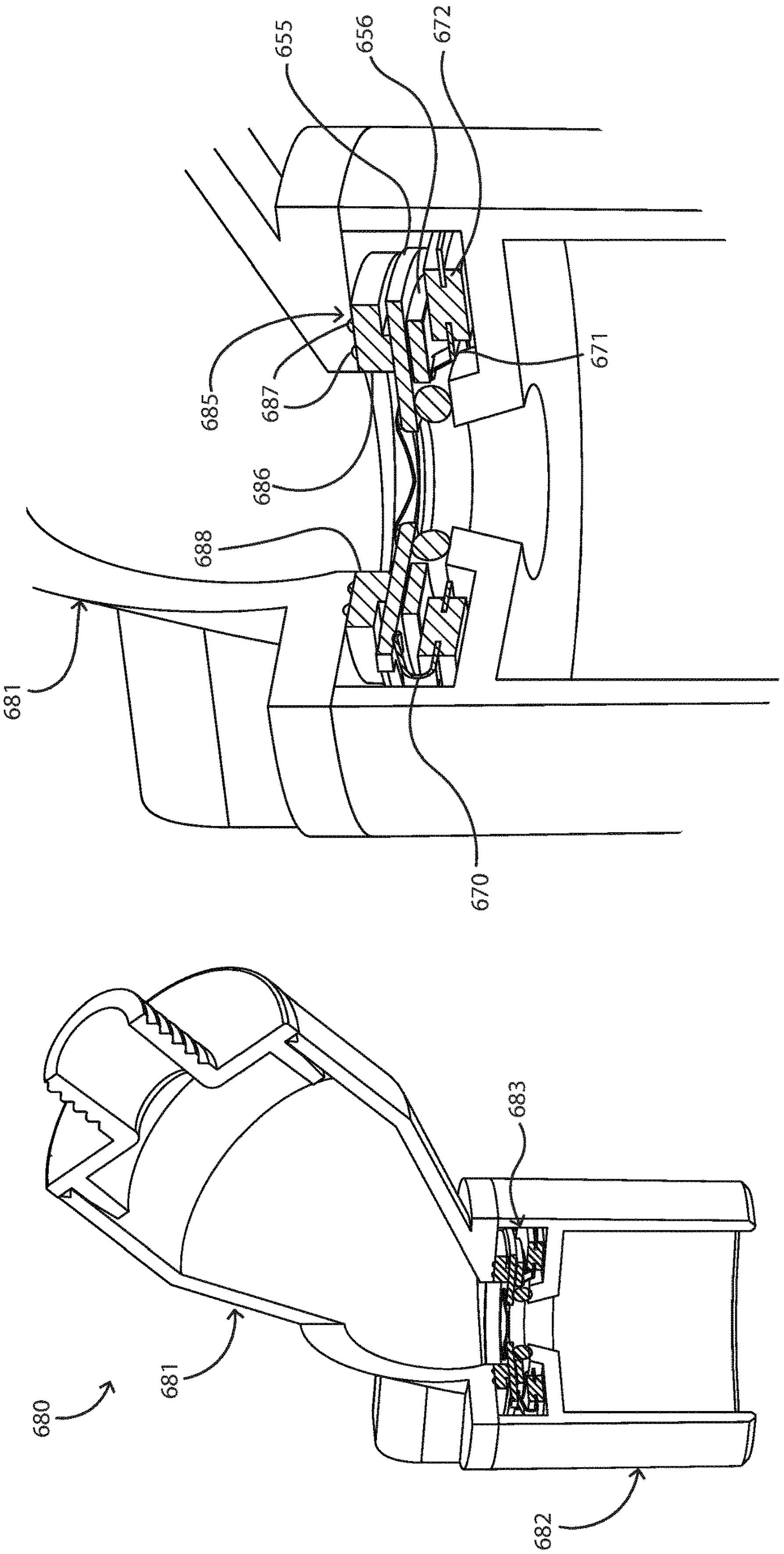
Figure 22:
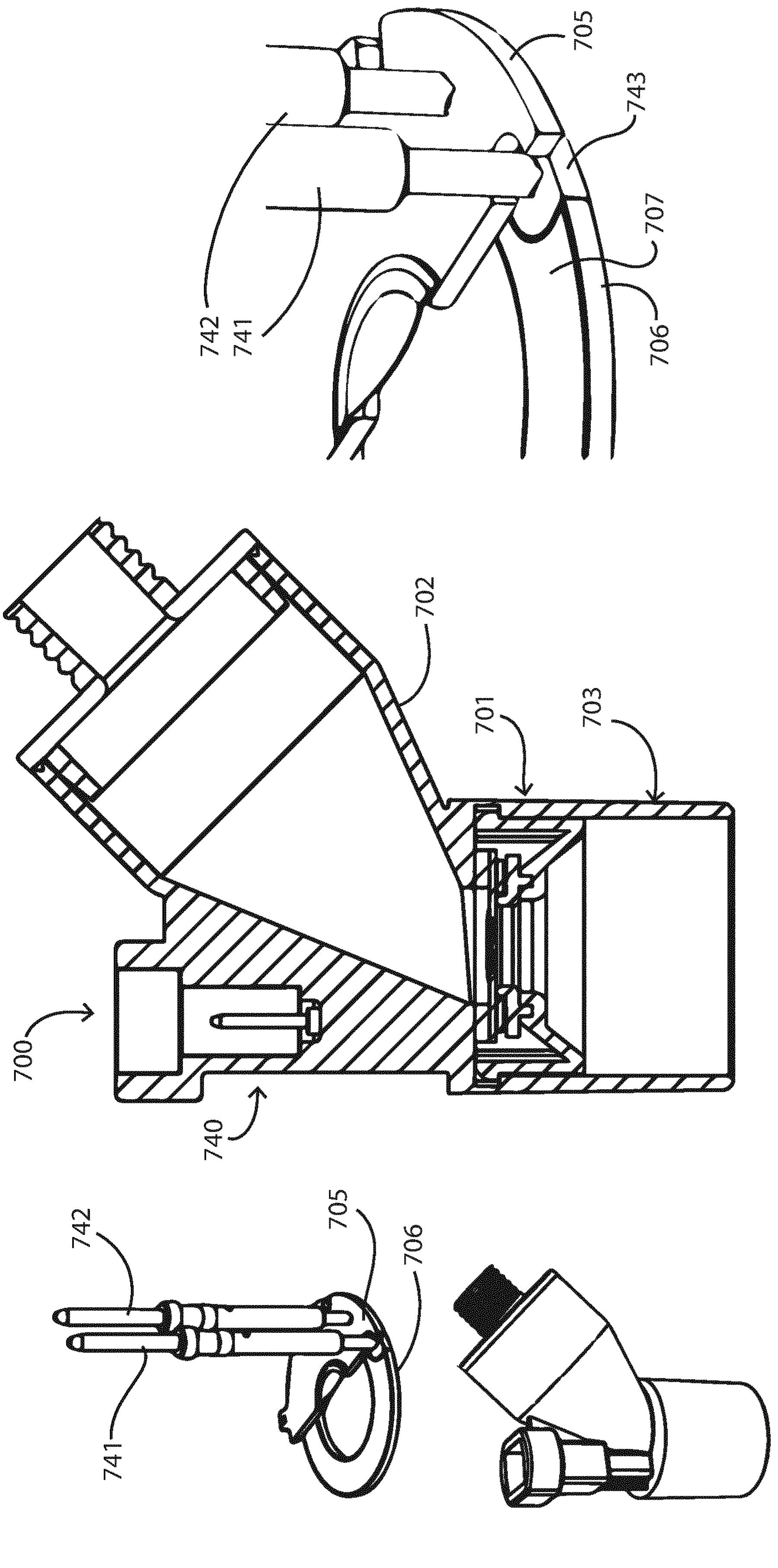
Figure 23:
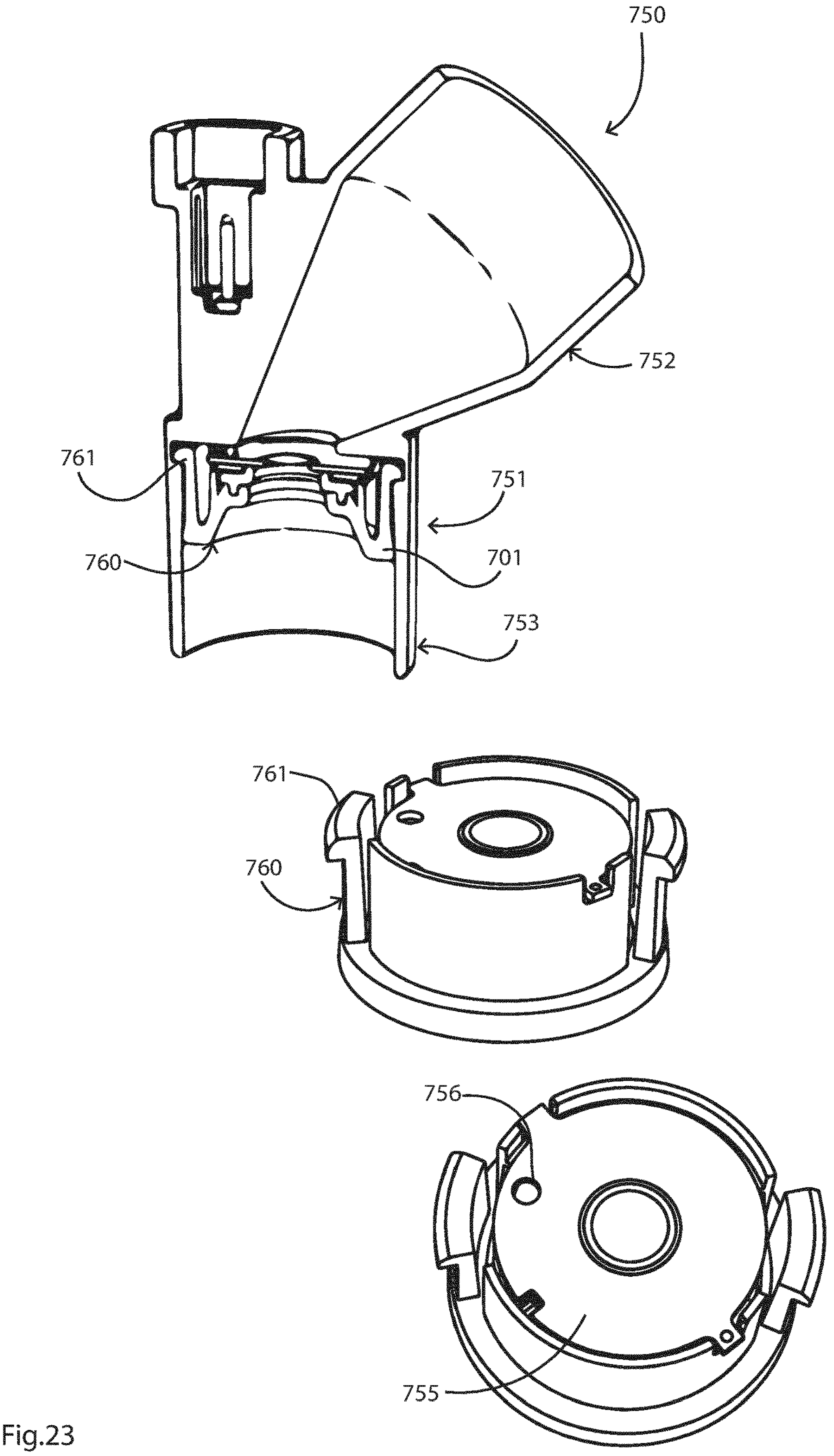
Figure 24:
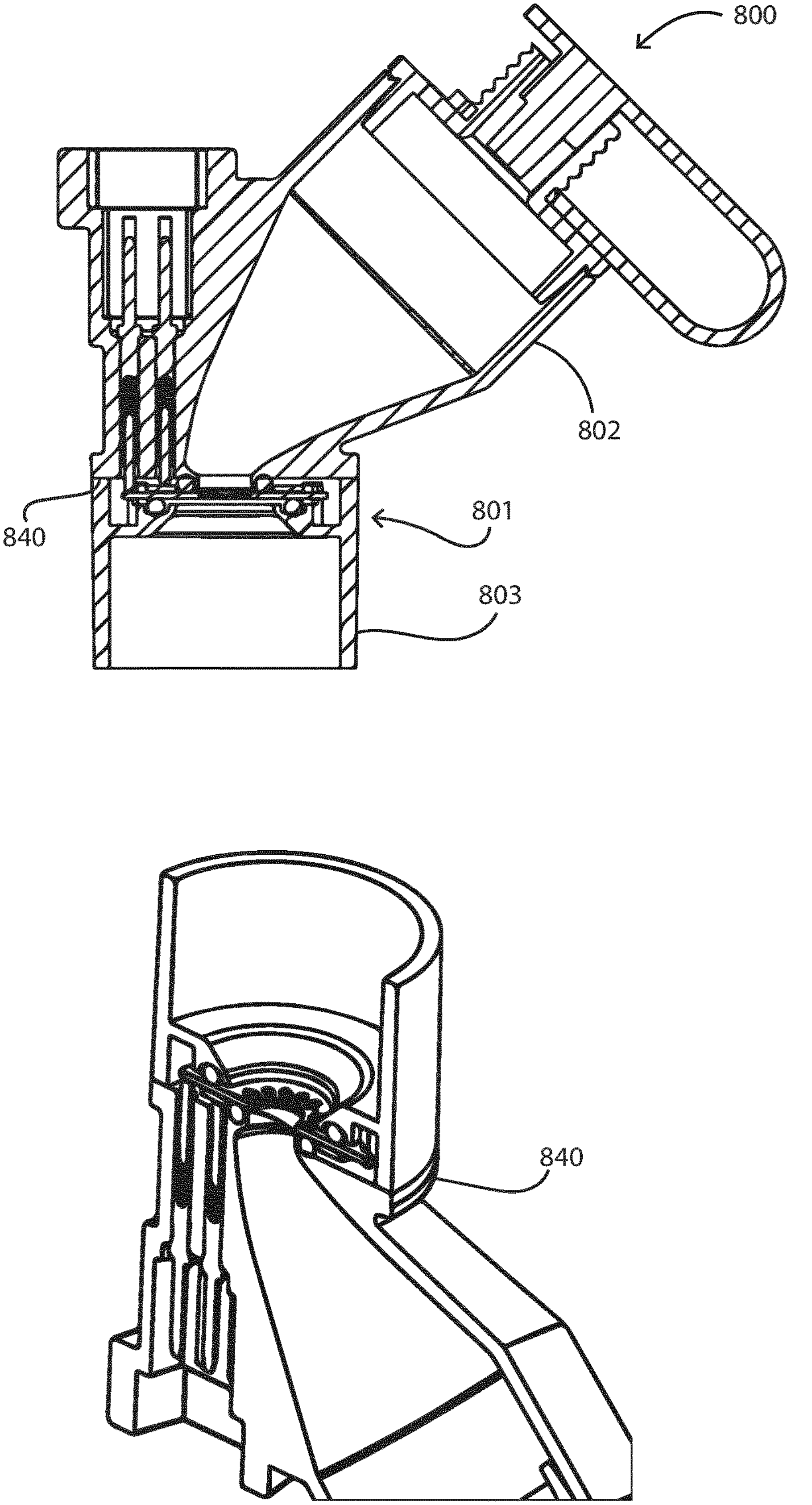
Figure 25:
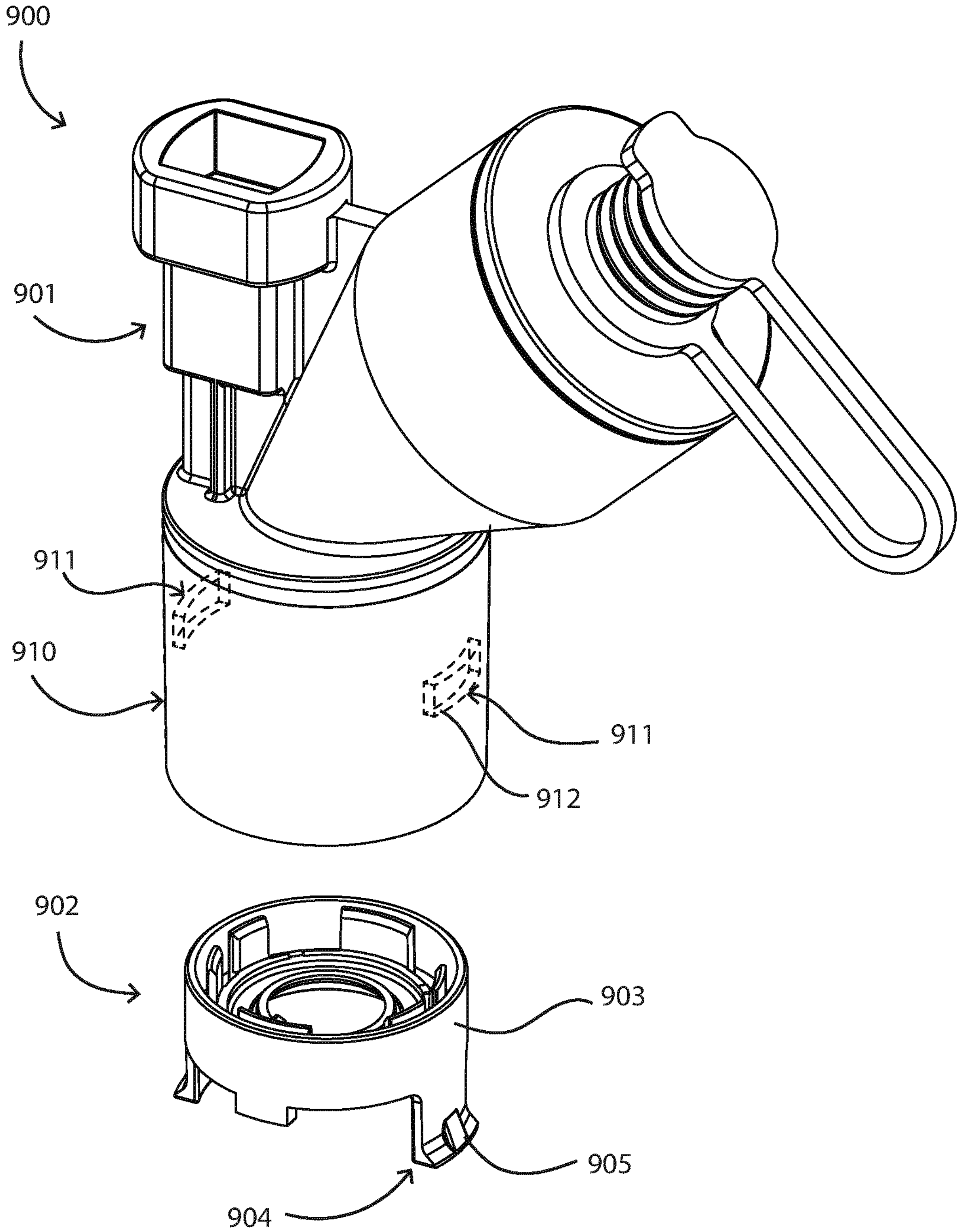
Figure 26:
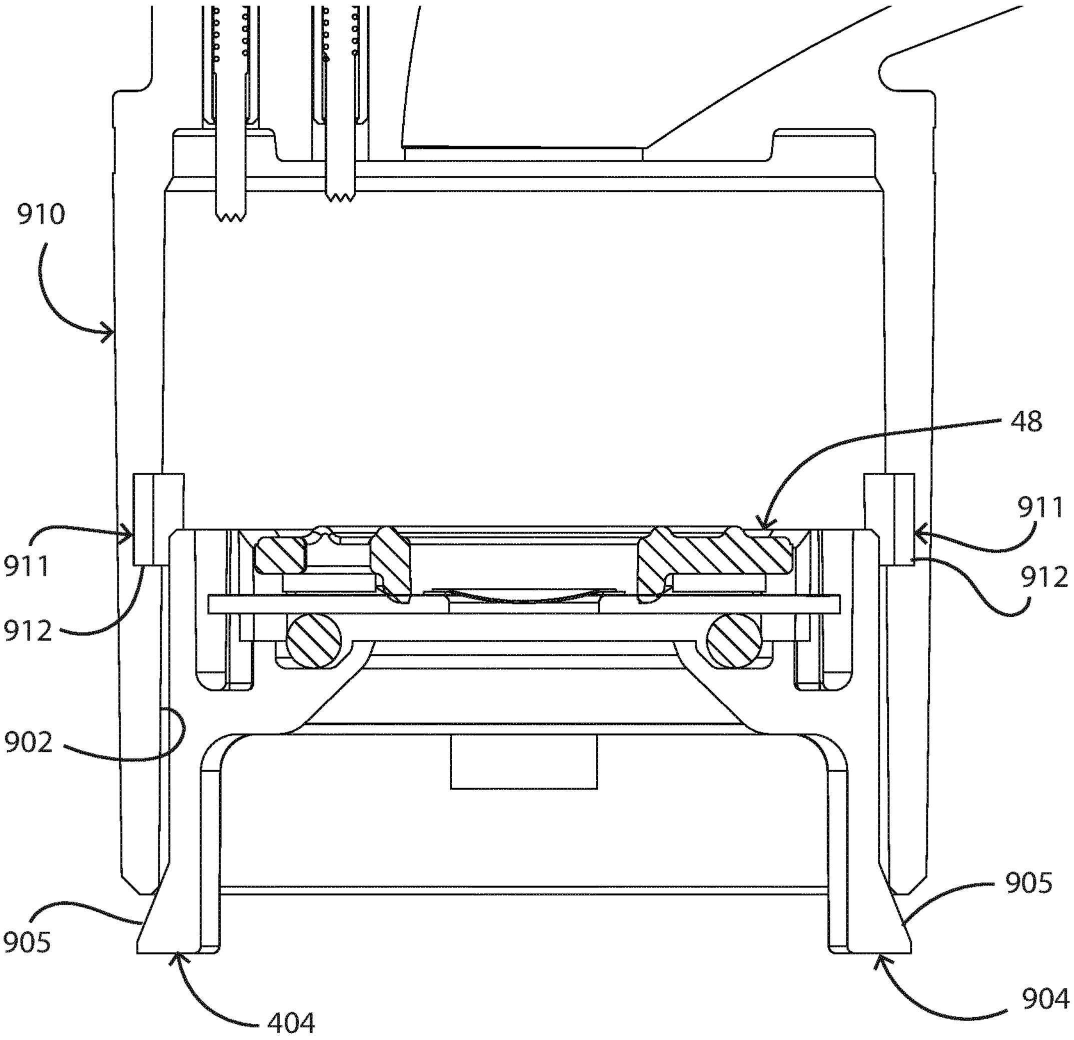
Figure 27:
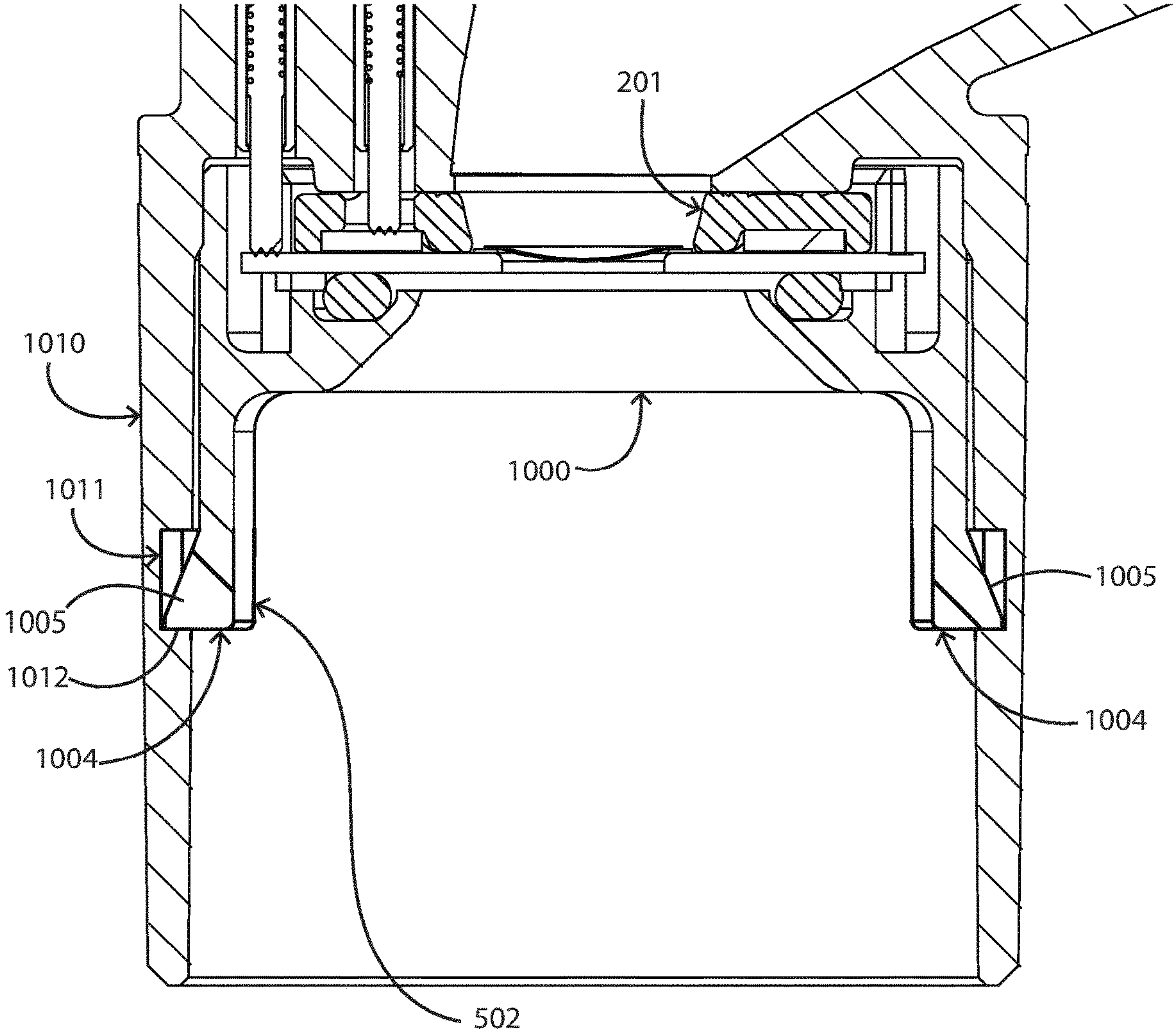
Figure 28:
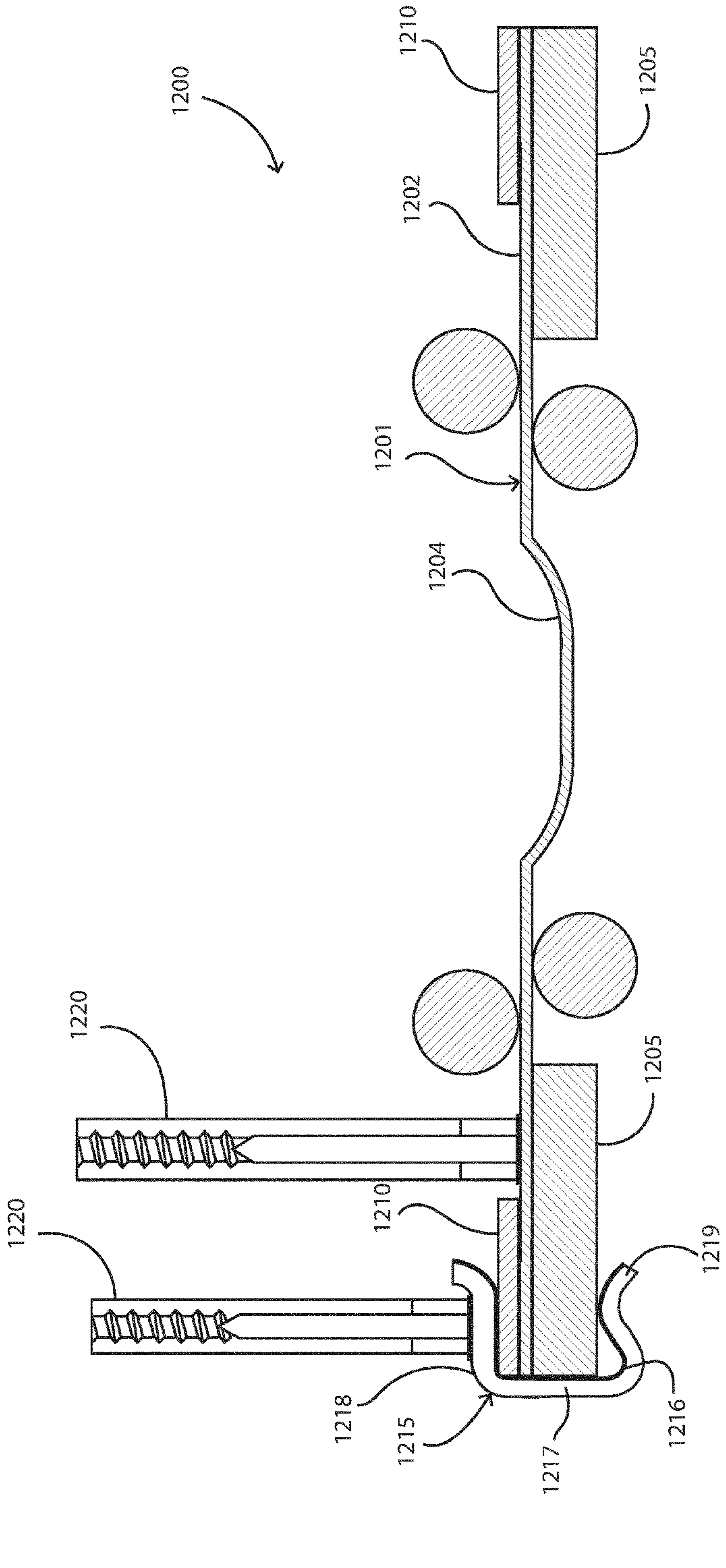

FIGS. 9 and 10 inclusive are views equivalent to FIGS. 5 and 6 of an alternative nebulizer, with a gasket having a downwardly-depending rim;

FIGS. 11 to 14 are views equivalent to FIGS. 2, 3, 5, and 6 of a further alternative nebulizer, in this case with a gasket having a body which extends further radially to encompass the radially outer conducting pin;

FIG. 15 is a diagrammatic sectional view of a nebulizer having a reservoir with a hydrophilic coating on a surface exposed to liquid in use;

FIG. 16 is a diagrammatic sectional view of an aerosol generator of a nebulizer in which a piezoelectric vibration generator has a large internal diameter;

FIG. 17 is a diagrammatic sectional view and an exploded view showing a nebulizer with a piezoelectric vibration generator mounted to a downstream side of the support washer;

FIGS. 18, 19, 20, and 21(*a*) are sectional, exploded, and cut-away views showing an alternative nebulizer with a piezoelectric vibration generator on a downstream side of a support washer, power to the piezo being provided by a spring contact assembly, and FIG. 21(*b*) shows a variation on the aerosol generator of FIG. 21(*a*), in this case having a different top seal;

FIG. 22 is a set of perspective and diagrammatic sectional views showing an alternative nebulizer with a piezoelectric vibration generator ("piezo") on a downstream side of the washer, in this case driven by conducting spring pins;

FIG. 23 is a set of cut-away and perspective views of an alternative nebulizer with a retaining clip for ease of assembly;

FIG. 24 is a pair of diagrammatic sectional views showing a nebulizer with an ultrasonic weld between housing parts;

FIG. 25 is a perspective view of a nebulizer of an alternative embodiment, with the aerosol generator shown outside of the housing, and FIG. 26 is a diagrammatic cross-sectional view showing the aerosol generator being inserted to show function of ramps in retainer toes;

FIG. 27 is a diagrammatic cross-sectional view of an alternative nebulizer with ramp features of the FIG. 25 nebulizer but in this case having a wider gasket; and FIG. 28 is a diagrammatic cross-sectional view of an alternative aerosol generator, having a vibration drive on a downstream side of a support and two upstream-side spring pins for conducting power to the drive.

DESCRIPTION OF THE EMBODIMENTS

We describe aperture plate nebulizers which have a liquid vessel delivering liquid onto an aperture plate with apertures in the micro-metre size range, preferably directly by gravity, in which the vessel or reservoir is configured to provide a throat over the aperture plate ("AP"). The reservoir has features for reduction of bubble formation and consistent and predictable flow of liquid on the reservoir side of the AP. One such feature is a throat size which is too large for significant bubble formation. Preferably, the throat size has an area in the plane of the AP of at least 18 $mm^2$, more preferably at least 20 $mm^2$, more preferably at least 25 $mm^2$, more preferably at least 30 $mm^2$. In one example the throat area is about 34 $mm^2$, and is preferably in the range of in the range of about 32 $mm^2$ to 40 $mm^2$.

It is preferred that the throat area is at least twice the active area (the portion of the AP which vibrates, inside the attachment rim) of the aperture plate. In one example the AP is of electroformed metal with a diameter of 3.50 mm and an area of 9.6 $mm^2$. In this case the throat area is preferably at least 20 $mm^2$.

The aerosol generator may be of the type having a washer-shaped support to which is attached an annular piezoelectric vibration generating device on either the upstream or downstream side, and the aperture plate is connected by, for example, brazing to the internal rim of the support. The attachment of the AP to the support washer may alternatively be by adhesive, as described in our published patent specification WO2019/115221, the contents of which are incorporated by reference. In general, the AP has a rim which is attached to the support, and inside the rim there is the active portion, i.e. the portion which vibrates.

The aperture plate may have a main body (the vibratable, active, portion) with apertures of approximately 6 μm diameter and with a density of approximately 90 per mm in cross section (if the manufacturing uses photo-defined masking the density may be much higher, in the order of thousands per mm as described for example in WO2012/092163). Around this body there is the rim having a lower surface attached to the support washer. The AP is directly supported on the support washer laterally internally of the resilient seals and the vibratory drive piezo, without any mechanical clamping. There may be grooves in the surface of the AP rim, which assist adherence.

The AP rim may be micro-machined in the lower surface to have multiple parallel anchor grooves each groove having a pair of side surfaces and a base surface, the base surface being substantially in the plane of the AP. The grooves are in the lower surface, extend generally in the radial direction, and have a zig-zag pattern as viewed in plan, with straight lengths between bends. In this example of adhesive attachment, in general, it is preferred to have as high a density of grooves as possible, consistent with maintaining sufficient mechanical strength in the aperture plate, especially at the rim where it is attached to the washer. For example, there may be 72 grooves in one example, and it is preferred that there are in the range of 30 to 130 grooves.

In general, it is preferred that, where there is adhesive attachment instead of brazing, anchor grooves are provided having a depth in the range of 10 μm to 40 μm, a width in the range of 20 μm to 150 μm, an angular pitch in the range of 2.5° to 12.5°, and that they have at least one bend in direction, and each bend is at an angle in the range of 45° to 120°, and preferably in the range of 80° to 105°. Adhesive is applied to the rim on the underneath side between the rim and the washer. The washer is sloped away from the plane of the aperture plate with a convex curvature as viewed in cross-section. Advantageously, the adhesive forms a fillet where the washer bends away from the lower surface of the aperture plate. This provides excellent mechanical strength with integration of the washer to the aperture plate.

There is a gasket between the vessel housing and the aerosol generator at the AP support on the upstream side, the gasket having a rim extending between the support and the housing in the axial/longitudinal direction (parallel to the axis of the aperture plate), and a lateral portion extending radially to overlie at least some of the support. The configuration is such what when axial pressure is applied during manufacture the gasket tends to deflect radially outwardly, creating a tapered slope on the inside surface of the central opening in the gasket. This provides a throat shape around at least some of the circumference of the throat. The housing configuration preferably provides a reservoir internal surface which forms a continuation of the gasket opening internal surface. This provides a throat funnel shape formed by a combination of the gasket opening inner surface and the housing reservoir internal surface. Such a funnel shape may be provided by a top gasket which does not extend radially to a large extent, in some examples not extending as far as the piezo drive. In one such example it only extends radially to the extent of an inner rim which forms the gasket opening. This gasket internal liquid-contacting exposed surface is preferably not overhung by the housing and may be textured in a manner as described below for low propensity to bubble formation on the surface. Additionally or alternatively, there may be a hydrophilic coating on one or both of the gasket internal exposed surface and the reservoir surface.

By having different components in contact with the liquid, the gasket and the housing, it is convenient to provide a combination of surface types to optimise liquid flow to the AP, with minimization of bubble formation.

Preferably the gasket is supported together with the aerosol generator as a unitary assembly mounted on a retainer which engages as a unit with the remainder of the housing. This action is preferably movement towards the liquid supply chamber (reservoir) until a snap-fitting engagement of the retainer in place with the gasket axially compressed against the housing around the throat. The gasket is accurately and concentrically seated in an annular seat of the retainer, and this is preferably provided by resilient tabs which are arc-shaped and spaced-apart around the circumference of the gasket seat.

Figure 1:
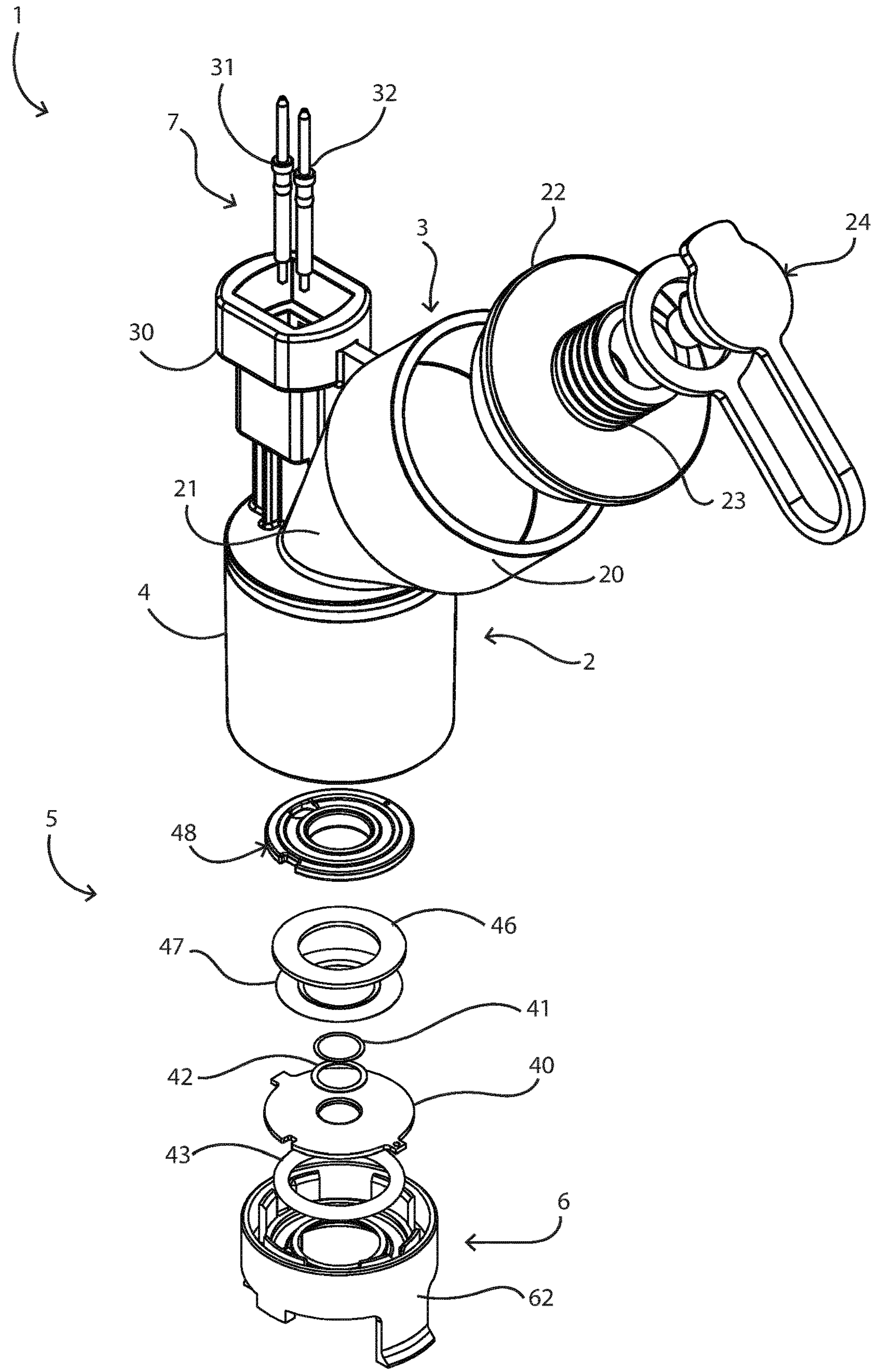
FIG. 1 is a perspective exploded view of a nebulizer.

Referring to FIG. 1 the following main components of a nebulizer 1 are illustrated:

2, integral plastics housing body,

3, liquid supply chamber (or "reservoir"),

4, aerosol delivery tubular outlet,

5, aerosol generator assembly,

6, retainer, supporting the aerosol generator 5 in the integral housing body 2;

20, reservoir tubular top part,

21, reservoir funnel-shaped lower part ("funnel"),

22, liquid supply chamber cap;

23, cap tubular opening,

24, cap silicone plug,

30, power conducting pin support part of the housing body 2;

31, 32 conducting pins extending through the pin support housing part 30;

The reservoir top part 20 is in fluid communication with the inclined funnel-shaped lower part ("funnel") 21 for delivering liquid onto the aperture plate ("AP"). The aerosol delivery tubular outlet 4 is below the AP, is integral with the reservoir parts, and is co-axial with the AP. The axis of the funnel 21 is inclined to the AP axis. This allows use of the nebulizer at a wide range of orientations with gravity fall of the liquid onto the AP.

The conducting pins 31 and 32 are for conducting power to a piezoelectric vibration generator of the aerosol generator, and are retained within, and guided by, the pin housing part 30 of the housing body 2.

The retainer 6 is for carrying the aerosol generator assembly 5, pressed against a lower surface of the funnel 21. The aerosol generator assembly 5 comprises, from top down, an upstream seal namely a gasket 48, a piezoelectric vibration generator ("piezo") 46, an adhesive ring 47 under the piezo 46, an aperture plate 41, a braze ring 42, an annular washer-shaped aerosol generator support ("washer") 40, and a downstream O-ring 43. This assembly is supported by the retainer 6 and is surrounded by the aerosol delivery tube 4. The piezo adhesive ring 47, while shown for illustrative purposes as a discrete item is in fact bonded between the piezo 46 and the washer 40, attaching the piezo to the washer in a manner which conducts electrical power to the underside of the piezo 46. Likewise, the braze ring 42 is an integral part of the rim of the aperture plate ("AP") 41 and the internal rim of the washer 40, attaching the AP to the washer. In other examples the attachment of the AP may be bonded rather than brazed. This example involves an electroformed aperture plate 41 with "hourglass" shaped apertures. However, in other examples the aperture plate may be formed by photo-defined technology as described in our prior patent specification nos. WO2012/092163 or WO2013/186031. There may be a reservoir layer of liquid supply cavities over the aerosol-forming apertures, formed in a manner for example as described in WO2012/092163 or WO2013/186031, and these may have a diameter in the range of 20 μm to 400 μm The aperture plate 41 apertures have an outlet opening diameter in the range of 1 μm to 10 μm, and in one example about 2 μm to 3 μm.

Figure 2:
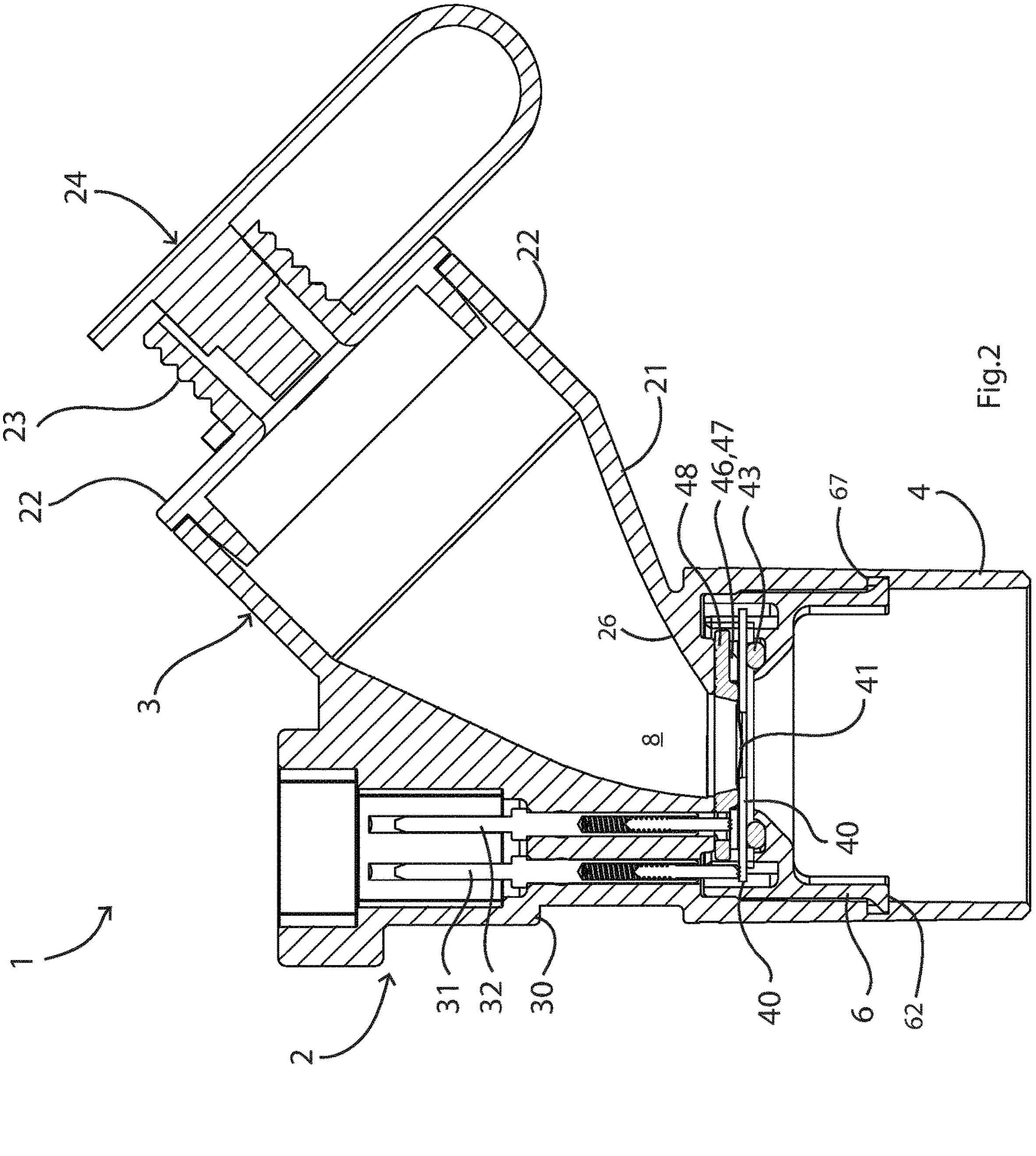
FIG. 2 is a sectional elevational view of the nebulizer.
Figure 3:
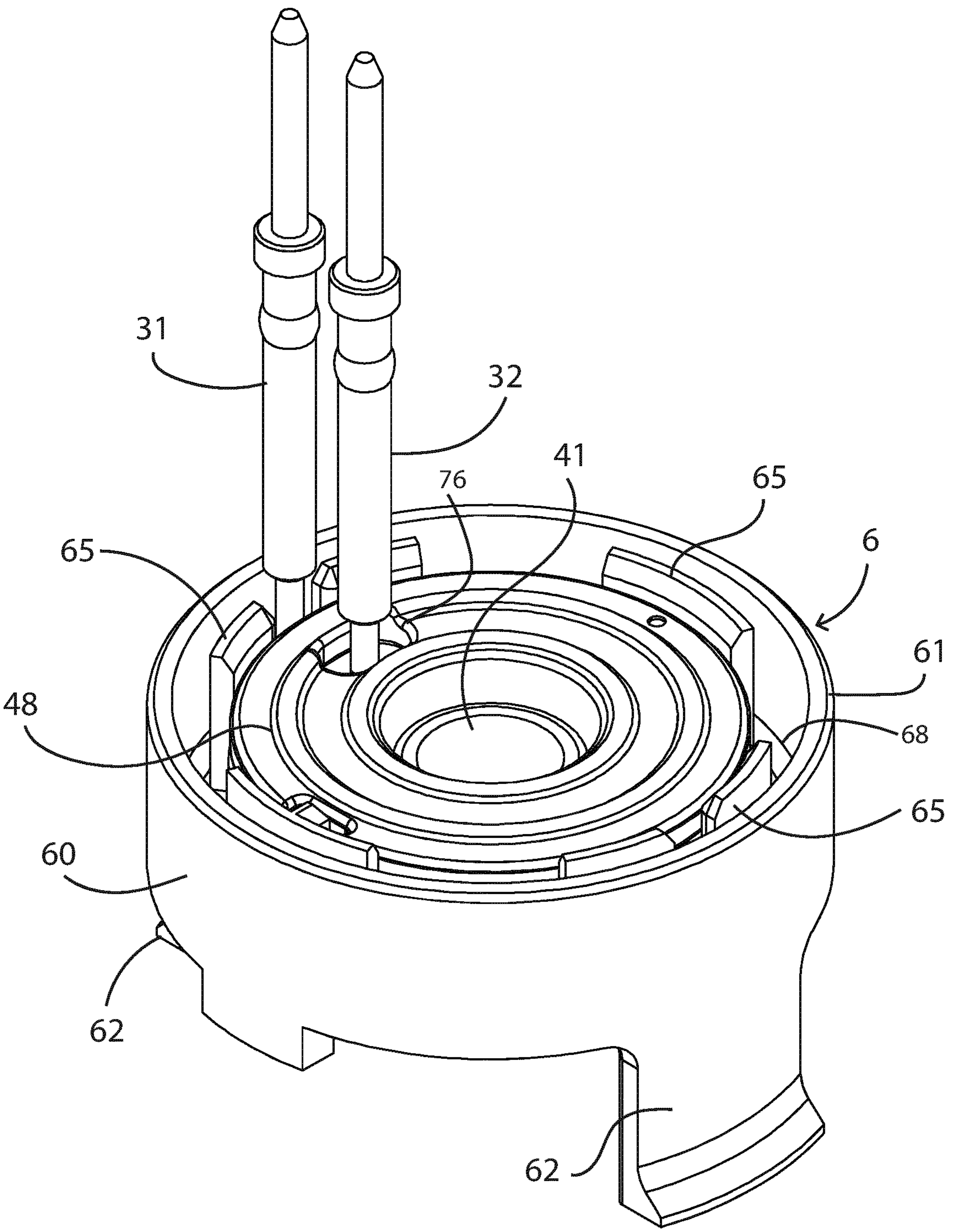
FIG. 3 is a perspective view of the aerosol generator when removed from the housing.
Figure 4A:
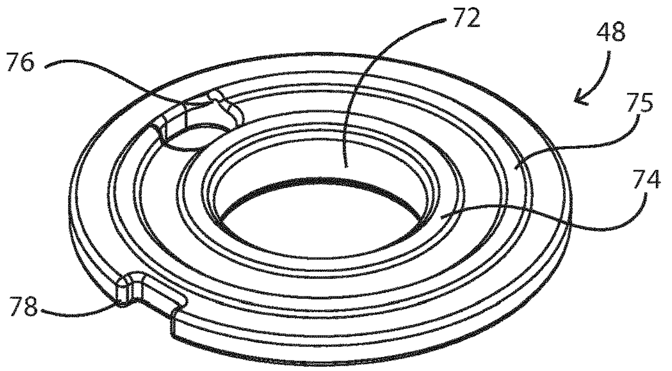
FIG. 4 is a set of views of a top gasket of the aerosol generator.
Figure 4B:
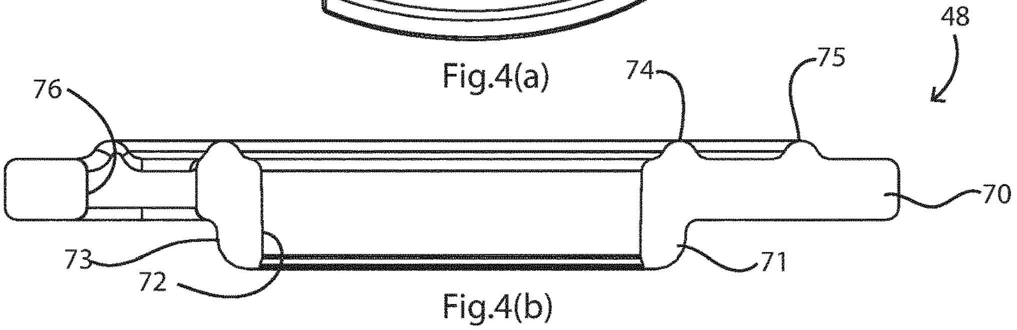
Figure 4C:
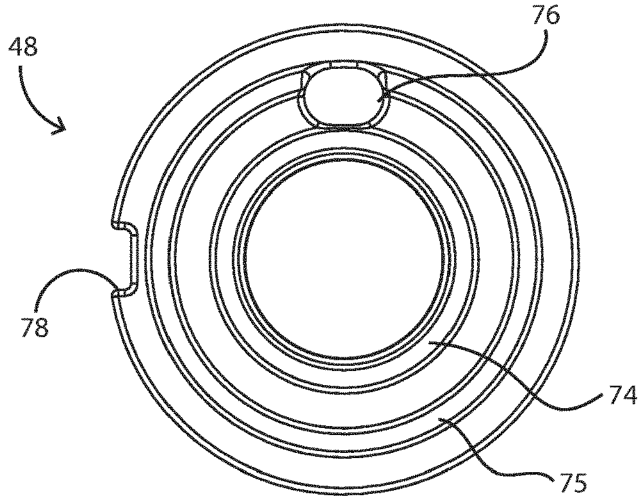
Figure 4D:
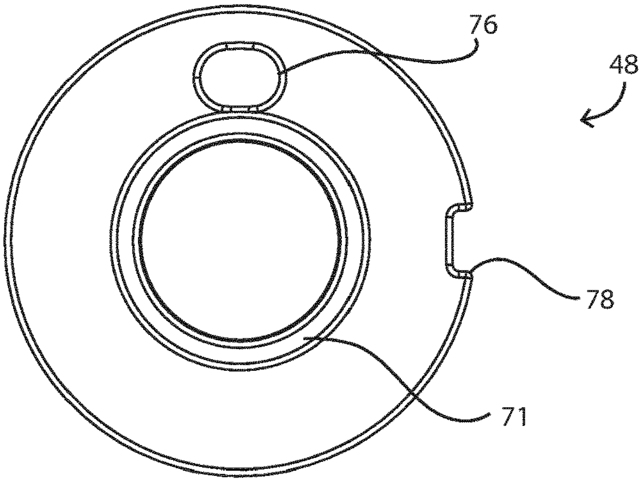

Referring also to FIGS. 2 and 3, the retainer 6 is configured so as to securely support and contain the components of the aerosol generator assembly 5. It has a circumferential wall 60 with a top rim 61 and a pair of lower depending legs 62 with toes which snap fit as clips into corresponding recesses 67 of the aerosol outlet tube 4. At the upper end, a series of circumferentially-extending elongate tabs 65 define the outer surface of a circular seat for the gasket 48, and FIG. 3 shows the gasket 48 retained within the tabs 65 in a concentric position.

The retainer 60 also forms an annular seat 68 for the downstream O-ring 43, shown most clearly in FIGS. 5 and 6. The washer 40 is supported underneath by the O-ring 43 housed within the groove 68 of the retainer 6, the washer 40 resting on the O-ring 43 and itself supporting the piezo 46 adhered to the washer 40 top surface. The AP 41 is attached by the braze ring 42 to the washer 40.

The liquid supply reservoir funnel 21 has an internal tapered surface 26 inclined inwardly towards the AP 41, defining a throat 8 over the AP together with the gasket inner surface 72. The latter is not overhung by the housing, forming a continuation of the housing surface. By having two components, the gasket and the housing, it is convenient and versatile to provide a combination of surface types to optimise liquid flow to the AP, with minimization of bubble formation.

The housing 21 forms a continuation of the gasket 48 inner surface 72, so that they together provide a liquid flow funnel towards the AP. As described in more detail below, this allows not only smooth and streamlined flow, but also allows the provision of a different surface near the AP, by for example a desired roughness of the gasket surface 72 for optimisation of flow characteristics and/or bubble prevention. The reservoir 3 is tilted away from the axis of the AP, and forms a much greater angle to the AP axis on the lower side. On the lower side, the funnel wall 26 diverges away from the throat area at an angle to axial preferably greater than 45° and more preferably greater than 50° and still more preferably greater than 55° for at least some of the circumference of the throat. In this particular example the angle is about 60° at its greatest. This provides a maximum amount of space over the AP, thereby minimising surface area for bubble growth, as described in more detail below.

The compressed axial (aperture plate central longitudinal axis) dimension distance between the plane of the rim of the aperture plate and the bend in the housing where it is splayed out is 2.3 mm, and is more generally preferably in the range of 1.8 mm and 3.0 mm. This provides splaying out a short enough distance from the AP to help minimise bubble prevention. The fact that about 1.8 mm of this dimension is provided by the gasket inner surface is helpful, as it may have a desired surface roughness to additionally prevent bubble formation. In general, it is preferred that the axial dimension of the gasket at the throat is in the range of 1.5 mm to 3.0 mm.

The top (upstream) gasket 48 is sandwiched between and compressed by the washer 40 and the bottom surface of the housing body funnel 21. The gasket 48 counterbalances the force from the O-ring 43 and from the pins 31 and 32.

As shown particularly in FIG. 4 the gasket 48 comprises a body 70 of material moulded to form a downstream-depending circular rim 71 with the internal surface 72 forming an opening, which is part of the throat 8, for liquid supply to the AP. The rim 71 provides a gasket depth which is greater than the depth of the remainder of the body 70, and because it forms part of the opening surface 72, it extends this opening surface in the downstream direction. In this example the depth of the rim 71 below the body 70 is 0.8 mm, and in general it is preferred that it is in the range of 0.5 mm to 1.1 mm. The body extends in the radial (lateral) direction to provide a washer annular shape in general outline, and so it thereby interfaces between a number of components, such as between the piezo 46 and the reservoir 21, and between the support 40 and the housing 21. It therefore provides sealing and balance within the aerosol generating core.

The gasket body 70 is also an integral base for inner and outer concentric circular top ridges 74 and 75 extending in the upstream direction for contact with the housing reservoir. These have a height of 0.3 mm and in general it is preferred that they have a height in the range of 0.1 mm to 0.5 mm. There is a through hole 76 in the body 70 to receive the radially inner conducting pin 32. There is also a slot 78 in the outer edge of the body 70 for mistake-proofing the assembly. It prevents the seal being loaded into the retainer if it is not in the correct annular orientation.

The gasket 48 is of medical grade liquid silicone rubber supplied as two component compounds which are mixed together and injected into a hot mould to cure. In general, it is preferred that the gasket has a Shore hardness in the range of 20-80 Shore A, more preferably in the range of 30 to 60 Shore A.

The dimensions of the gasket 48 are in this case, when relaxed:

- internal diameter, 6.2 mm;
- external diameter, 14.7 mm;
- maximum depth, 2.1 mm;
- height of ridges 74 and 75, 0.3 mm;
- height of ridge 71 with respect to the body 70, 0.6 mm.

In this example the throat 8 is about 6.0 mm diameter, as defined by the opening 72 of the gasket 48 at its lower end closest to the AP. This large diameter throat reduces risk of bubble entrapment due to air ingestion.

The gasket 48 is tolerant to dimensional variation of plastics housing components from the point of view of sealing, protecting the piezo 46 and the electrical connections.

The gasket 48 is located on the retainer 6 during automated assembly, as shown in FIG. 3. This allows accurate placement and automated manufacturing, which is particularly important for accurate location of the gasket relative to the aerosol generator 5 components.

Referring again to FIGS. 5 and 6, the positions before and after full insertion of the retainer 6 are shown, in which the retainer 6 and the aerosol generator 5 are provided as a sub-assembly, and are pushed upwardly against the funnel 21 lower surface. As is clear from FIG. 6, in the final position the legs 62 are snap-fitted into the notches 67 of the aerosol outlet tube 5, at which position the downstream O-ring 43 and the gasket 48 are slightly compressed axially. Hence, the manufacturing process can be efficient and tolerant of small placement variations. It is simple to axially load the components of the aerosol generator 5 (as best shown aligned for manufacture in FIG. 1), and to then press them axially upwardly against the housing wall 21 lower surface. This is a robust method of seal location. FIGS. 5 and 6 also show a diverging surface 69 downstream of the throat 8, for aerosol flow from the AP.

The throat 8 diameter of about 6.2 mm is achieved through the opening 72 diameter of the gasket 48. As shown in FIG. 6, there is a tapering of the opening due to the axial compression, providing a funnel shape. The diameter narrows and at the downstream extremity may be in the range of 0.1 mm to 0.3 mm less than the nominal 6.2 mm diameter when the gasket is relaxed.

The tapering of the opening is contributed to by the rim 71 protruding downwardly and being much more deformable than the body 70.

Physical Support and Sealing Benefits for the Aerosol Generator 5

The aerosol generator 5 is under vertical compression across a large area, providing an excellent seal which is more tolerant to dimensional variation of the plastics housing components. The upper ridges 74 and 75 compress with the axial compression as shown in FIG. 6, providing grip and robust stability in the high frequency environment, in which the plate may be vibrating at for example 128 kHz.

Moreover, the gasket 48 covers the piezo 46, thereby limiting the potential for ingress of moisture from the funnel 21 at the throat 8 area to the electrically-conductive components 31, 32, 46, and 40.

Referring again to FIG. 6, it will be clear from this diagram that the gasket 48 provides a large degree of counterbalancing of forces which arise from pressing by the conducting pins 31 and 32 against the piezo 46 and the washer 40. This is contributed to by the large bulk of the gasket's body 70 and large surface abutting the underside of the funnel 21. Moreover, the gasket 48 acts as a cover over the piezo 46, thereby helping to protect it from ingress of moisture in the highly humid and high-frequency environment.

The pair of upper ridges 74 and 75 are particularly beneficial because they ensure uniform contact with the funnel 21 all around the gasket's periphery, but are not so high that they prevent contact by the remainder of the upper surface of the gasket when under axial compression.

Bubble Prevention

The gasket 48 has in this example a fine textured surface finish with arithmetic roughness average, Ra, in the range of 1.6 μm to 3.2 μm. The roughness average parameter Ra is defined in ISO4287:1998+A1:2009 at 4.2.1. Ra is calculated by measuring the average length between the peaks and valleys and the deviation from the mean line on the entire surface within the sampling length. Ra averages all peaks and valleys of the roughness profile and then neutralizes outlier points so that they have no significant impact on the final results The Ra range of 1.6 μm to 3.2 μm is equivalent to 24 to 30 on the VDI 3400 (Charmilles) surface roughness scale ("VDI").

Referring to FIG. 8 the surfaces of two gaskets are shown with a magnification of 1000. The gasket on the left has a surface finish roughness of average of about 1.8 μm, and the gasket on the right-hand side has a surface finish with a roughness average of about 2 μm to about 3 μm. The surface roughness is more visible in the surfaces facing the camera as they are in focus. It is possible to be more accurate about roughness of the left-hand gasket because it is moulded, and surface roughness of the mould steel is accurately known.

Such a surface roughness helps to prevent small bubbles from adhering for a significant time to the internal gasket surface, and hence helps to prevent bubbles from combining. It is preferred that the scale of magnitude of the roughness is comparable to that of the bubbles which tend to congregate and coalesce above the rim of the AP (aperture size 2 μm to 6 μm, and vibration frequency of about 128 kHz. A surface roughness Ra value of 1.6 μm to 3.2 μm is particularly effective for an aperture plate aperture diameter in the range of about 1 μm to 6 μm, and/or a vibration frequency in the range of about 60 kHz to 200 kHz, more preferably in the range of 100 kHz to 160 kHz.

FIG. 7 shows bubbles which naturally develop on the upper surface of the AP, especially around its rim, due to air being drawn up thorough the apertures due to the AP vibration at a frequency of 128 kHz. We have found that a surface roughness value of Ra in the range of about 1.6 μm to 3.2 μm is better than a smoother surface. Bubbles rising from the AP tend to be less likely to stagnate on the surface of the gasket.

The desired surface roughness may be achieved in any desired manner. The image on the left of FIG. 8 is of a gasket formed by injection moulding, and on the right by 3D printing.

The gasket may for example be moulded from a thermoplastics elastomer material such as those grades supplied by BASF, or as mentioned above by additive manufacturing technologies (3D printing).

There is excellent liquid flow to the AP due to the reservoir having an internal smooth funnel surface leading into a softer material with a higher surface roughness.

In other embodiments the gasket and/or the funnel are coated with a hydrophilic coating, to further reduce risk of bubble stagnation and coalescence. The hydrophilic coating would be thin enough not to affect the surface roughness, but would deter bubbles from coalescing. The hydrophilic coating preferably has a thickness in the range of 0.5 μm to 2.0 μm.

In various examples the hydrophilic coating may be of a monomer composition with vinyl acetate, hexamethyldisiloxane (HMDSO) mixed with oxygen in a given ratio with more HMDSO than $O_2$.

Alternative Gasket Configurations

Referring to FIGS. 9 and 10 a nebulizer 200 has a gasket 201 instead of the gasket 48, and all other components are the same and are indicated by the same reference numerals. The gasket 201 has a downwardly-depending rim 202 around its outer edge, at a radial position between that of the two pins 31 and 32. This has the benefit of increasing the extent of enclosure around the piezo, and of contact with the vibrating surfaces, both the washer and the funnel 21. The enveloping on both radial sides and the top side of the piezo helps to ensure reliability even if there is a slight leak of moisture into the space over the washer due to a gap evolving between the retainer and the housing.

Figure 12:
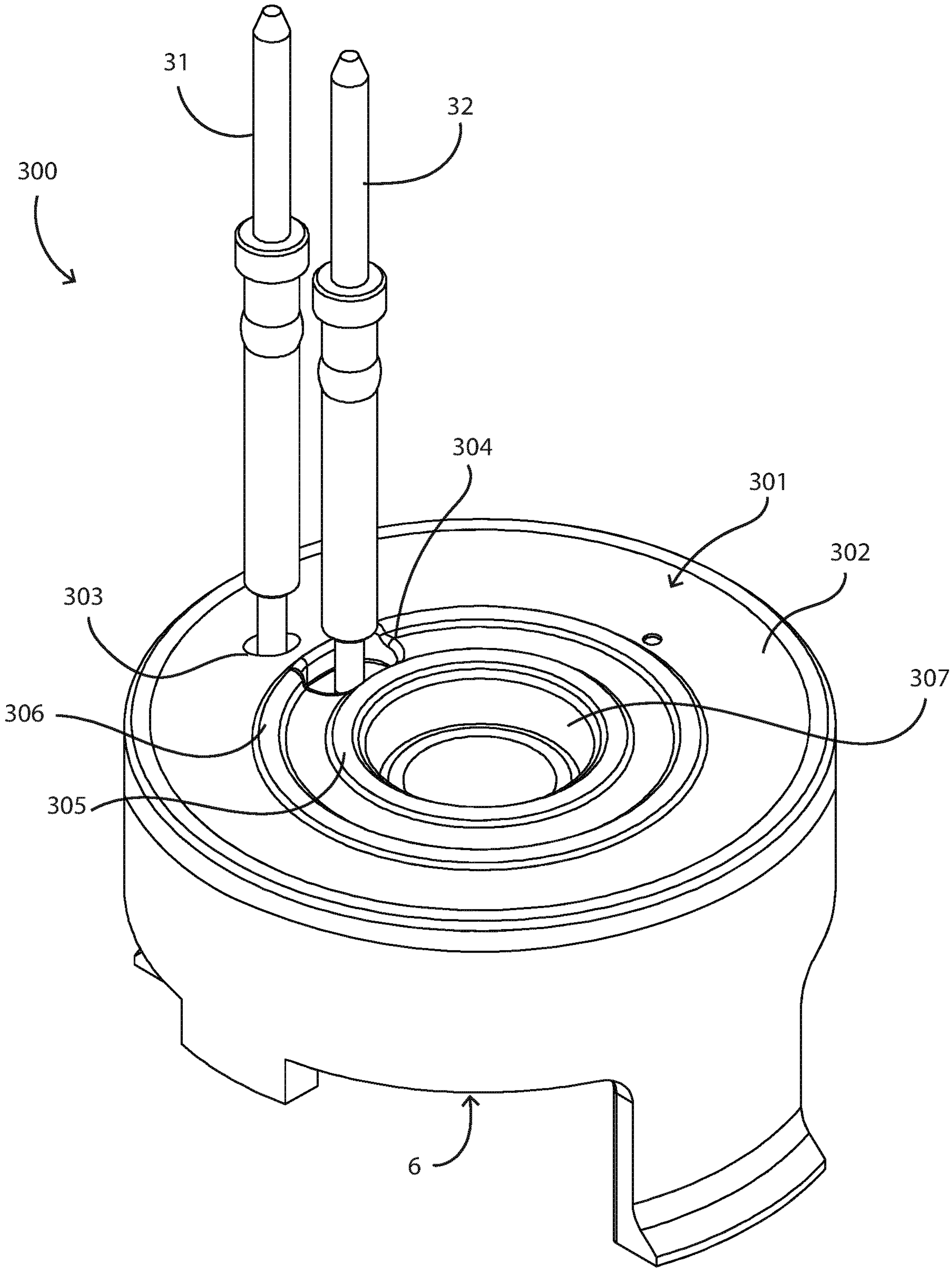
Figure 13:
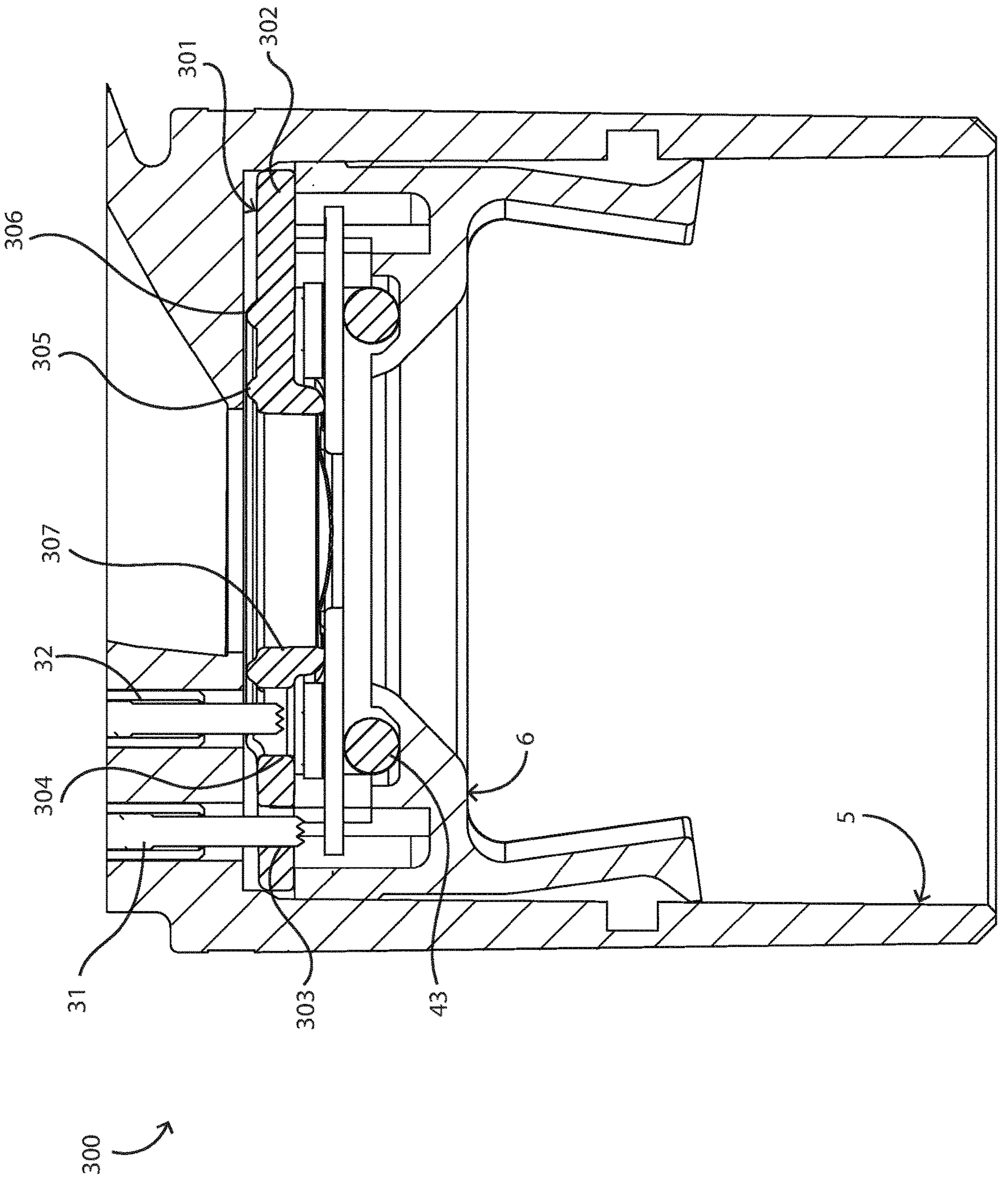
Figure 14:
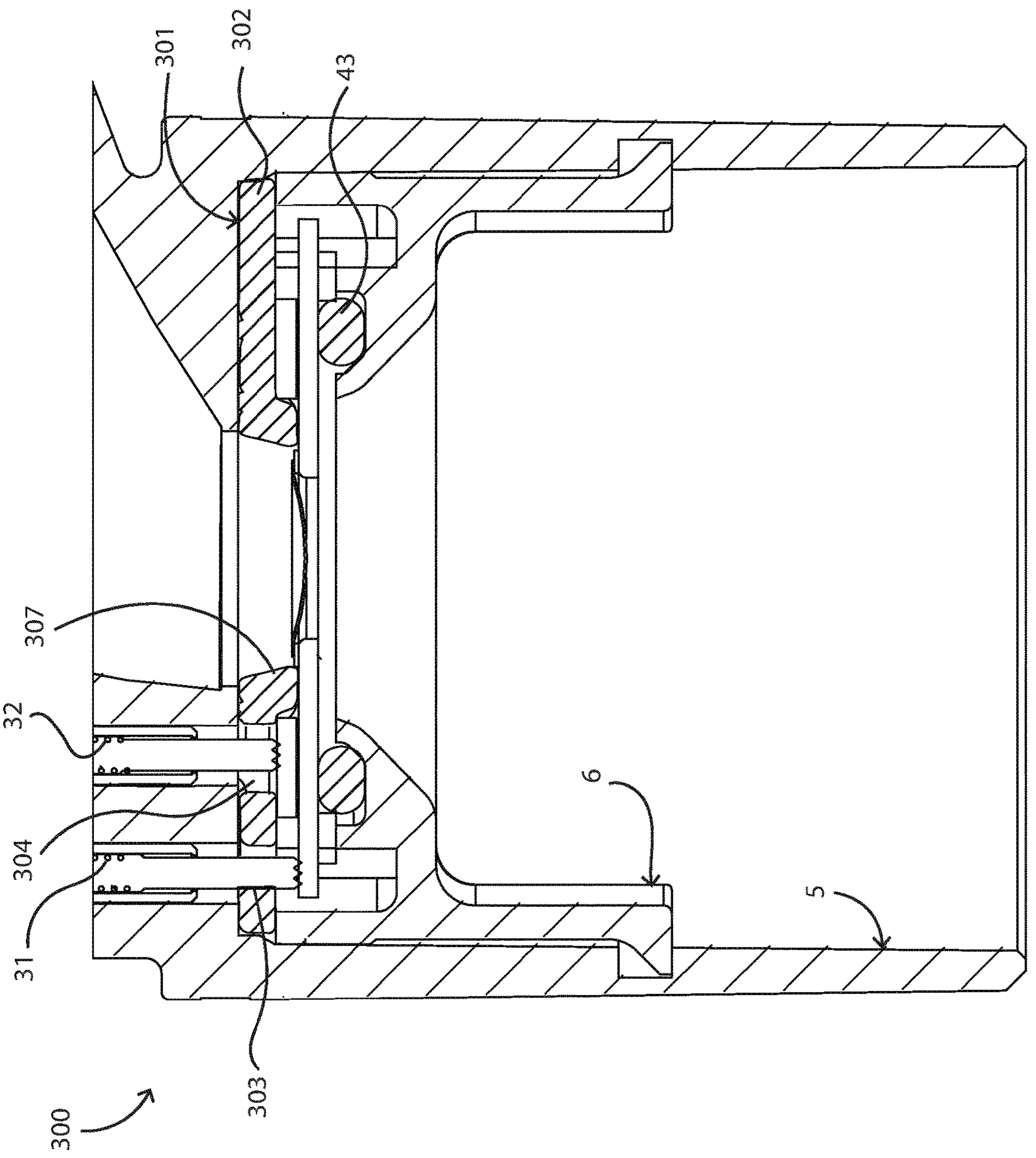

Referring to FIGS. 11 to 14 an alternative nebulizer, 300, has a gasket 301 instead of the gasket 48, and again the other components are the same and indicated by the same reference numerals. The gasket 301 has a body 302 extending further radially, and has an aperture 303 for the radially outer pin 31 in addition to an aperture 304 for the pin 32. There are upstream ridges 305 and 306 which are similar to the ridges 74 and 75 of the gasket 48. The gasket body 302 extends radially sufficiently far to engage at its peripheral edge the housing 5. The gasket 301 has an opening surface 307 which forms part of the throat over the AP, as best shown in FIGS. 12 and 14.

This arrangement has the benefit of providing greater surface contact area on the top. Also, it provides a resilient seal between the two mating plastics parts, the retainer and the reservoir/housing.

It is envisaged that in other examples the gasket may have a downwardly-depending rim akin to that of the gasket 201 and a top surface area and radial extent akin to that of the gasket 301.

The invention is not limited to the embodiments described but may be varied in construction and detail. For example, the throat area may have an area greater than 34 $mm^2$.

In various alternative examples the throat may have a hydrophilic coating to reduce tendency of micro bubbles stagnating on the throat surface and coalescing and forming large bubbles.

The annular vibration generator ("piezo") may have a larger internal diameter than in the above embodiments, for example in the region of 10 mm in diameter, thereby providing more space for a larger throat.

Also, the vibration generator may be attached to the downstream side of the support washer, thereby providing more space over the AP for a wide throat area. In this case there may be conducting pins on opposed sides of the piezo, or there may be soldered electrical connections, or one or two resilient clip terminals. Alternatively, there may be conducting pins arranged as in the nebulizer, but the vibration generator extends around an outer rim of the support washer. In other examples the electrical pins extend through a slot in the washer onto a wraparound electrode on the piezo.

For minimizing bubble enlargement, the nebulizer may have one or more of the following features:

- Hydrophilic surfaces exposed to the throat, possibly with surface modification of the reservoir body.
- Larger throat achieved by increasing the inner diameter of the piezo, and/or mounting the piezo on the downstream side of the washer.
- Spring electrical contacts, possibly with a side entry arrangement.
- Spring conducting pins providing electrical power, in some examples with the pins extending through a hole in washer.
- Use of a retainer clip for components of the aerosol generator.
- An ultrasonically welded base Hydrophilic Coating FIG. 15 is a diagrammatic sectional view of a nebulizer 500 having an aerosol generator 501 in a housing having a reservoir 502 with a hydrophilic coating 504 on a surface exposed to liquid in the throat. The hydrophilic coating parameters are as set out above for the previous example with a hydrophilic coating. This diagram illustrates where such a coating may advantageously be applied.

The hydrophilic surface may be achieved for example by applying textures to the housing such as by laser etching to achieve a fine pattern. Alternatively, there may be post-mould treatment such as by plasma treatment or sputtering.

Wider Throat

FIG. 16 is a diagrammatic sectional view of an aerosol generator 551 of a nebulizer 550 having a reservoir 552, and an outlet tube 553. There is a washer 555 supported underneath (downstream side) by an O-ring 556 and on the top (upstream) side by an O-ring 557, in which a piezoelectric vibration generator has a large internal diameter. In this arrangement there is a 7 mm throat inner diameter achieved by a piezo 559 having a larger size than in previous embodiments, inner diameter 10.8 mm and outer diameter 14.5 mm in this case. Also, there is a top O-ring 557 having an inner diameter of 7.5 mm and an outer diameter of 10.5 mm Spring Contact Assembly FIG. 17 is a diagrammatic sectional view and an exploded view showing a nebulizer 600 with an aerosol generator 601, a reservoir 602, and an outlet tube 603. In this case the piezoelectric vibration generator (606) is mounted to a downstream side of the support washer (605). In order from upstream towards downstream there are:

- reservoir 602,
- upstream O-ring resilient support 608,
- a core assembly with a combined washer 605 and piezo 606,
- a spring contact assembly 607 having clips 615 for contacting the piezo and clips 616 for
- extending around the edge of the support and contacting its top surface, and
- downstream part of the housing (aerosol outlet conduit) 603.

In this case power is provided to the piezo 606 by the spring contact assembly 607, which receives power from pins 620 physically connected to the assembly 607. The assembly 607 spring contacts contact the piezo (which is underneath the washer) directly and the separate contacts 616 receive power from the other pin 620 which contact the washer directly for conduction of power via the washer to the opposed side of the piezo.

Figure 18:
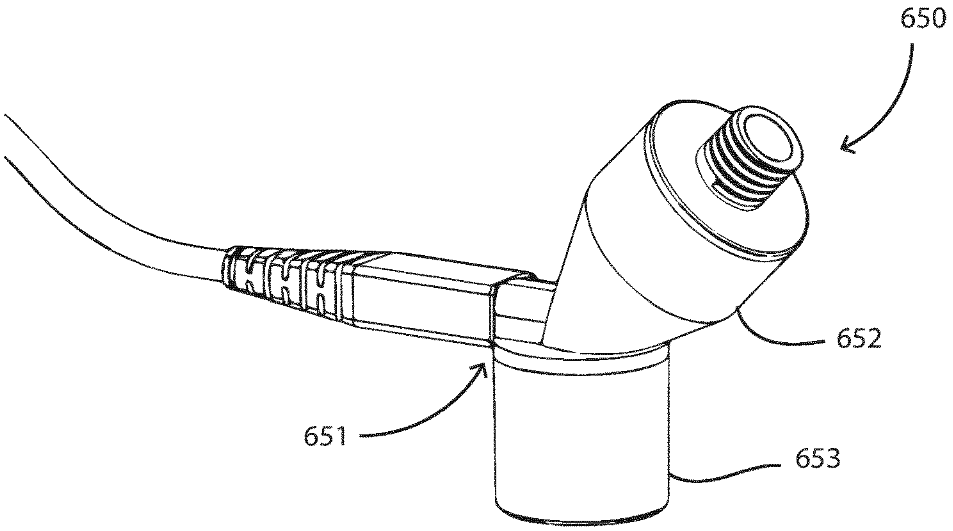
Figure 18:
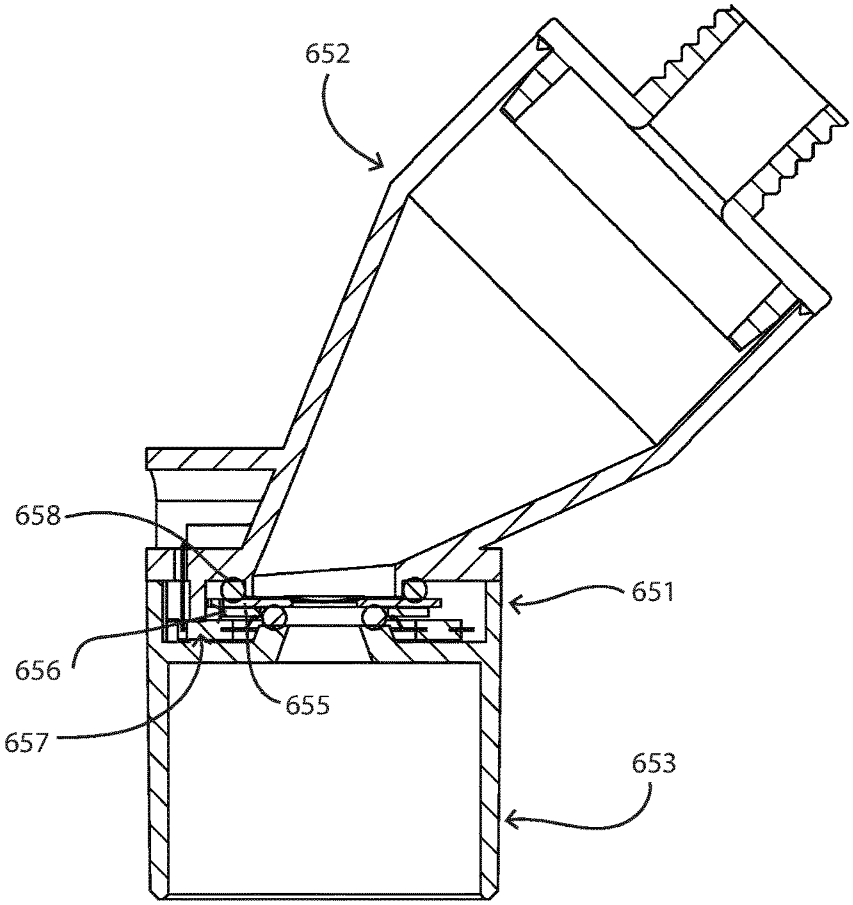
Figure 19:
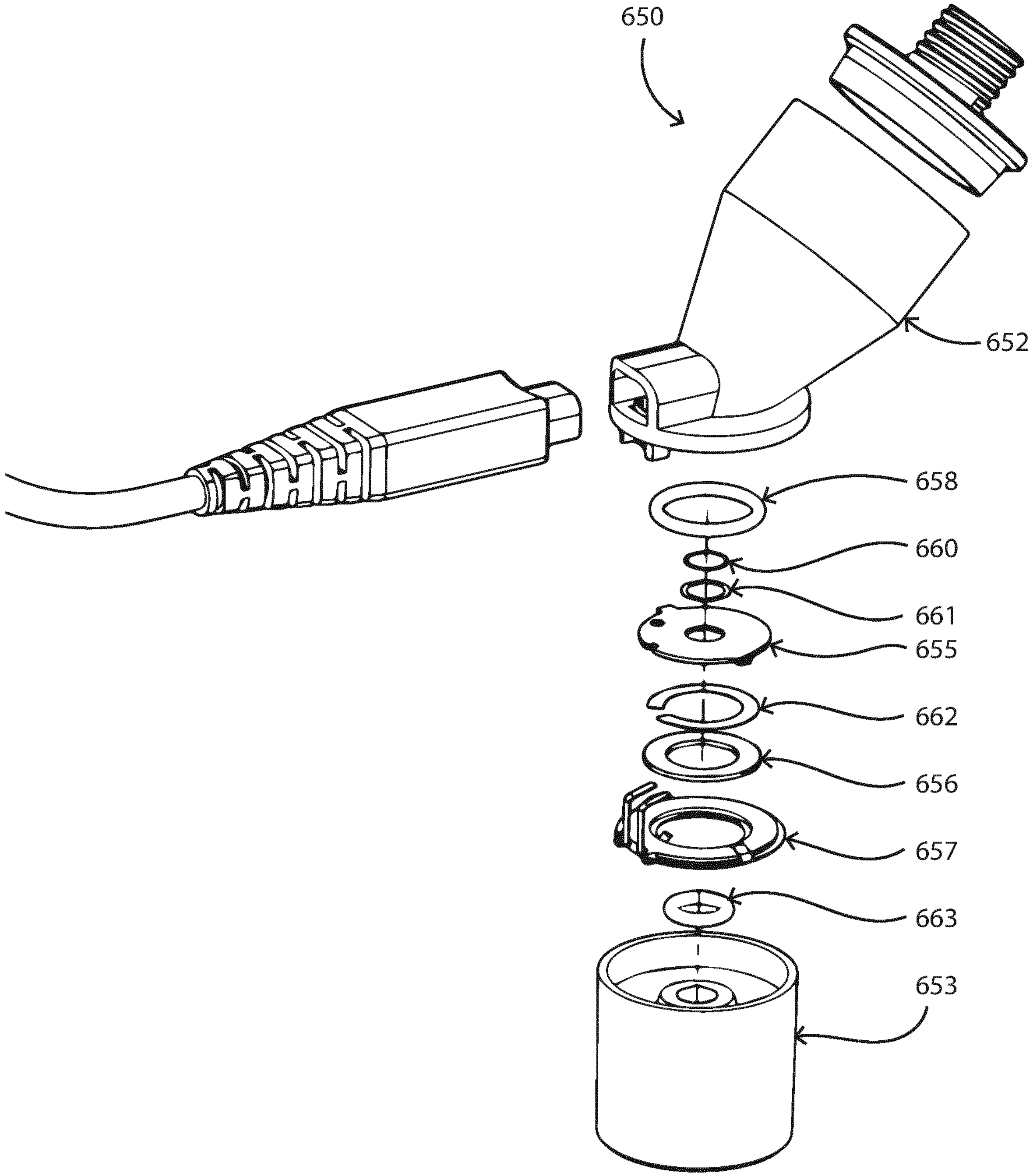

FIGS. 18, 19, 20, and 21 are views as follows of an alternative nebulizer 650:

FIG. 18, perspective and diagrammatic sectional,

FIG. 19 exploded,

FIG. 20 enlarged cut-away perspective, and

FIG. 21(*a*) enlarged cut-away perspective.

In FIGS. 20 and 21(*a*), only the piezo, washer and O-rings are hatched where cut-away. The nebulizer 650 has an aerosol generator 651, a reservoir 652, and an aerosol outlet 653. A piezoelectric vibration generator 656 is on a downstream side of a support washer 655, and power to the piezo is provided by a spring contact assembly 657. In this case the throat has a diameter of 9 mm. In order, from upstream to downstream, the nebulizer comprises:

reservoir 652,
upstream O-ring seal 658,
aperture plate 660,
braze ring 661,
washer 655,
conductive adhesive 662,
piezo 656,
spring contact assembly 657,
downstream resilient seal O-ring 663, having a smaller diameter than the upstream
resilient seal 658, and
aerosol outlet 653.

As shown most clearly in FIG. 20 the assembly 657 has upstanding electrical terminals 675 and 676 for contact with electrical supply conductors, not shown. The connection to the terminals 675 and 676 may for example be soldered, or alternatively or additionally crimped. FIGS. 20 and 21(*a*) show more detail of how electrical power is transferred to the piezo 656. There are spring terminals 670 extending around a rim of the spring contact assembly 657 to engage an exposed underside of the washer 655, and a resilient ridge 671 extending in the upstream direction to engage the underside of the piezo 656, which itself is on the downstream side of the washer 655.

A spring contact assembly such as illustrated provides considerable advantages because of the versatility in choice of mutual location for the vibration generator and its support. The spring contacts may in other examples be different, for example with a ridge-like conductor contacting the support in addition to or instead of the piezo. Likewise, a slip-like conductor may contact the piezo in addition to or instead of the support.

As shown in FIG. 21(*b*) a nebulizer 680 has a top housing 681 providing the funnel and a lower aerosol outlet part 682 which supports an aerosol generator assembly 683. In this case there is a top gasket 685, but other parts are the same as for the nebulizer 650 are assigned the same reference numerals. The top gasket 685 forms part of the throat over the AP with its internal opening surface being a continuation of the internal surface of the reservoir so that they together form the throat, and extends radially over part of the support washer 655. The annular piezo 656 is adhered by conductive adhesive to the underneath (downstream) side of the support 655, hence removing a component from above the support and leaving more scope for a wider throat area. This illustrates that a nebulizer with a top gasket as illustrated in FIGS. 1 to 14 may be employed with a spring assembly and piezo element mounted on the downstream side of the support.

Conducting Pins with Downstream-Mounted Piezo

FIG. 22 is a set of perspective and diagrammatic sectional views showing an alternative nebulizer 700 with an aerosol generator 701, a liquid supply reservoir 702 and an aerosol outlet tube 703. There is a piezo vibration generator 706 adhered to a downstream side of a support washer 705, in this case driven by conducting spring pins 741 and 742. The pin 741 extends through an aperture in the washer 705 to contact a terminal 743 at an upstream side of the piezo 706, and the pin 742 contacts the upstream surface of the washer 705 for conducting power to the top side of the piezo. This arrangement achieves a larger throat area due to the piezo being in the downstream side. It also allows spring pins to be used, which is particularly beneficial for transfer of power in a manner which is reliable in such an environment. Alternatively, the pin 741 may deliver power to the piezo downstream side via an electrode which extends around to the downstream side of the piezo.

Referring to FIG. 28, in another example an aerosol generator 1200 for a nebulizer comprises an integral support and membrane core 1201 having a support portion 1202 and a membrane 1204.

The core 1201 is supported by upper and lower O-ring seals, although any other suitable shape of resilient seal may be used. A piezoelectric annular element 1205 is adhered to the underside of the core 1201 around its outer edge, and on the opposed face of the core 201 there is an insulating annular ring 1210. Power is provided by a pair of conducting spring pins 1220, both on the top (upstream) side of the core and being parallel to each other. One pin 1220 provides power to the top surface of the core body 1202 for conduction of current through the body 1202 to the top surface of the piezo element 1205. Power is provided to the opposed, lower, surface of the piezo element 1205 by a conductive clip 1215 having two inwardly-sprung limbs 1218 and 1219 joined by a web 1217, the limbs acting like jaws to engage the other pin 1220 on its top surface, and engage the bottom surface of the piezo element 1205. The insulating ring 1210 and a coating around the core outer edge prevent electrical contact other than with the bottom surface of the piezo element 1205, the terminal clip 1215 extending around the outer edge to press together a sandwich of the insulator 1210, the core body 1202, and the piezo element 1205.

Advantageously, power is conducted around the web and the lower limb to engage the bottom surface of the piezo element. The insulating ring and a coating around the core outer edge prevent electrical contact of the clip other than with the bottom surface of the piezo element, the terminal extending around the outer edge to press together a sandwich of the insulator, the core body 202, and the piezo element.

Retaining Clip with Features Near the Aperture Plate Area

FIG. 23 shows a nebulizer 750 with an aerosol generator 751, a reservoir 752, and an aerosol outlet 753. There is a retaining clip 760 with spring clips 761 which extend in the upstream direction for snap-fit engagement at a location substantially co-planar with the aerosol generator. This retaining clip has a clipping direction which is reversed to facilitate assembly without over-travel, and to provide mechanical snap-fitting engagement closer to the aerosol generator.

Ultrasonic Weld Between Housing Parts

FIG. 24 shows a nebulizer 800 with an aerosol generator 801, a reservoir 802, and an aerosol outlet conduit 803. The reservoir 802 and the outlet 803 are joined by an ultrasonic weld 840 between the housing parts 802 and 803. This provides a particularly good seal.

Alternative Retainer

Referring to FIGS. 25 and 26 an alternative nebulizer 900 has a housing 901 with an aerosol outlet conduit 910 with a pair of opposed recesses 911 with lower edges 912. The retainer 902 has a tubular body 903 with a pair of opposed legs 904 with toes for snap-fitting in the opposed recesses 911, as for the other embodiments. However, in this case each leg 904 additionally has a ramp 905 facing radially outwardly, thereby assisting insertion of the retainer 902 during manufacture. This reduces the impact when the body is placed down over the retainer during assembly.

FIG. 27 shows a retainer 1000 having a main body 1002 with opposed legs 1004 with toes having ramps 1005. These snap-fit into recesses 1011 with lower edges 1012. In this case the gasket is the gasket 201, which extends fully radially over the piezo and as far as the housing and engages the support radially outwardly of the piezo.

It will be appreciated that the invention provides a nebulizer with many significant improvements arising from the upstream resilient seal in the examples where it has a surface exposed to, and forming part of, the throat. By this seal forming part of the throat in the reservoir and also acting as a seal it is a single part which performs two very important functions. It is particularly advantageous that there is no overhang by the housing over the exposed surface of the upstream resilient seal, providing a streamlined approach for liquid delivery to the aperture plate. Moreover, it is possible to modify the seal exposed surface to provide an enhanced benefit for bubble prevention, such as a roughened surface. It is particularly advantages in the examples of the seal exposed surface being funnel-shaped. Another major advantage is that the arrangement of the housing and the upstream seal allows a relatively wide throat, thereby contributing to predictable and efficient liquid flow to the aperture plate.

The invention is not limited to the embodiments described but may be varied in construction and detail. For example, the throat area may have an area greater than 34 $mm^2$. It is envisaged that in other examples the gasket may have a downwardly-depending rim akin to that of the gasket 201 and a top surface area and radial extent akin to that of the gasket 301. The downstream resilient seal may not be in the form of an O-ring. It may be a ridge of resilient material extending from the housing, and it may be affixed to the housing. It may have some features of the gasket, such as a body which extends radially outwardly to an extent greater than the O-ring as illustrated. It is also envisaged that in other examples the top gasket downstream-extending rim is not necessarily at the gasket opening, but could be radially outward from it by a small extent. It is also envisaged that the power conductor may include a combination of both spring contact(s) and conducting pin(s), although it is generally preferred that it be one or the other type.

It is also envisaged that the top gasket, where present, may only have a very limited body extending radially, but provides excellent advantages by way of resilient upstream support and also preferably roughness of the surface in contact with the liquid where it forms part of the funnel throat. In one example the gasket body only extends to approximately the radial extent of the ridge 74. In general, any of the features of nebulizers described herein may be employed in different combinations with other features than illustrated. Also, it is envisaged that the housing may be provided by a greater or lesser number of parts which interconnect together. For example, the aerosol outlet may be a discrete component which fits to the reservoir or to an intermediate housing component.

The invention claimed is:

1. A nebulizer, comprising:
a housing,
a liquid supply reservoir formed by the housing,
an aerosol outlet formed by the housing, and
an aerosol generator mounted within the housing and comprising:
a vibratable aperture plate,
an annular support supporting the aperture plate,
a vibration generator attached to the annular support,
a power conductor for transferring power to the vibration generator,
a downstream resilient seal mounted between the housing and the annular support on a side of the aperture plate opposed to the liquid supply reservoir, and
an upstream resilient seal mounted between the annular support and the liquid supply reservoir
wherein the power conductor comprises a first spring contact engaging an underside of the support or vibration generator on a downstream side of the support or vibration generator and a second spring contact engaging the underside of the vibration generator or support, the first and second spring contacts provide power delivery to the vibration generator, and
wherein at least one of the first spring contact and the second spring contact is configured to apply a spring force to the underside of the support or the vibration generator.

2. The nebulizer as claimed in claim 1, wherein the vibration generator is mounted to the downstream side of the support.

3. The nebulizer as claimed in claim 1, wherein the vibration generator is mounted to the downstream side of the support, and the second spring contact directly contacts the vibration generator.

4. The nebulizer as claimed in claim 1, wherein the support extends further radially than the vibration generator, and the first spring contact engages a surface of the support laterally of the vibration generator.

5. The nebulizer as claimed in claim 1, wherein at least one of the spring contacts is in the form of a resilient ridge which is arc-shaped in an axial, longitudinal view and the resilient ridge extends at least partly around the aperture plate.

6. The nebulizer as claimed in claim 1, wherein the spring contacts are mounted to a contact assembly which is mounted to the housing on a downstream side of the aperture plate.

7. The nebulizer as claimed in claim 1, wherein the vibration generator is mounted to the downstream side of the support; and wherein the power conductor comprises at least two conducting spring pins, on the upstream side of the aerosol generator.

8. The nebulizer as claimed in claim 1, wherein the vibration generator is mounted to a downstream side of the support; and wherein the power conductor further comprises at least two conducting spring pins, on the upstream side of the aerosol generator; and wherein a first spring pin of the at least two conducting spring pins engages an upstream-facing surface of the support and a second spring pin of the at least two conducting spring pins contacts an upstream-facing surface of the vibration generator; and wherein the second spring pin extends through an aperture of the annular support without conductively contacting the support.

9. The nebulizer as claimed in claim 1, wherein the vibration generator is mounted to a downstream side of the support; and wherein the power conductor further comprises at least two conducting spring pins, on the upstream side of the aerosol generator; and wherein a first spring pin of the at least two conducting spring pins engages an upstream-facing surface of the support and a second spring pin of the at least two conducting spring pins contacts an upstream-facing surface of the vibration generator; and wherein the second spring pin extends through an aperture of the annular support without conductively contacting the support; and wherein the first pin contacts the upstream surface of the support for conducting the power to an opposed side of the piezo which is isolated from an area of contact between the second pin and the vibration generator.

10. The nebulizer as claimed in claim 1, wherein the aerosol generator is mounted to a retainer and the retainer engages the housing.

11. The nebulizer as claimed in claim 1, wherein the aerosol generator is mounted to a retainer and the retainer engages the housing; and wherein the retainer comprises a retaining clip which extends in an upstream direction to engage the housing adjacent the aerosol generator.

12. The nebulizer as claimed in claim 1, wherein the aerosol generator is mounted to a retainer and the retainer engages the housing; and wherein the retainer comprises at least two ramps which are facing radially outwardly for guiding insertion of the retainer into the housing.

13. The nebulizer as claimed in claim 1, wherein the reservoir and the aerosol outlet are inter-connected by an ultrasonic weld.

14. The nebulizer as claimed in claim 1, wherein at least some of the surface of the reservoir has a hydrophilic coating.

15. The nebulizer as claimed in claim 1, wherein the vibration generator comprises a piezoelectric vibration generator having an internal diameter in excess of 6 mm; and wherein the upstream seal has an internal diameter in excess of 7 mm.

16. The nebulizer as claimed in claim 1, wherein the upstream resilient seal is in the form of a gasket having a body and a downstream-extending rim forming an opening, the body extending radially from the rim in a substantially annular shape, wherein the gasket comprises at least one upwardly-directed ridge for engagement with a housing surface, and wherein the gasket body overlies at least part of the annular support.

17. The nebulizer as claimed in claim 1, wherein the upstream resilient seal is in the form of a gasket having a body and a downstream-extending rim forming an opening, the body extending radially from the rim in a substantially annular shape, wherein the gasket comprises at least two upwardly-directed ridge for engagement with a housing surface, wherein the gasket body overlies at least part of the annular support, wherein at least one of the ridges is circular in plan, wherein the ridges have a height in the range of 0.1 mm and 0.5 mm, and wherein the downstream-extending rim has a depth relative to the gasket body in the range of 0.5 mm and 1.1 mm.

18. The nebulizer as claimed in claim 1, wherein the upstream resilient seal is configured so that when under an axial compression the upstream resilient seal forms an opening with an internal surface which is tapered inwardly in a flow direction to form a funnel shape at a throat over the aperture plate; and wherein some of the opening internal surface is formed by a downstream ridge of the upstream resilient seal; and wherein the gasket body overlies at least part of the vibration generator, the vibration generator being mounted to an upstream surface of the support.

19. The nebulizer as claimed in claim 1, wherein the aerosol generator is mounted to a retainer and the retainer engages the housing, wherein the retainer is snap-fitted within the aerosol outlet, and wherein engagement between the retainer and the aerosol outlet is assisted by compression and axial reactive force of the downstream resilient seal and the upstream resilient seal.

20. The nebulizer as claimed in claim 1, wherein the aerosol generator is mounted to a retainer and the retainer engages the housing, wherein the retainer is snap-fitted within the aerosol outlet, wherein engagement between the retainer and the aerosol outlet is assisted by compression and axial reactive force of the downstream resilient seal and the upstream resilient seal, wherein the retainer comprises an annular seat for the downstream resilient seal, wherein the support, the aperture plate, the vibration generator, and the upstream resilient seal are supported over the downstream resilient seal, and wherein the retainer forms an annular seat for the upstream resilient seal.

21. The nebulizer as claimed in claim 1, wherein the first and second spring contacts of the power conductor comprise a pair of conducing spring pins and one or both of the pins extends through an aperture in the upstream resilient seal; and wherein the upstream resilient seal has a Shore hardness in the range of 30 to 60 Shore A; and wherein the upstream resilient seal comprises a plurality of downstream ridges; and wherein the upstream resilient seal extends in the radial direction to form a gasket between plastics housing parts and extends in the radial direction to completely overlie the support.

22. The nebulizer as claimed in claim 1, wherein the upstream resilient seal has a surface exposed to the reservoir to form at least part of a throat over the aperture plate and has on at least some of the exposed surface a surface roughness average Ra in the range of 1.6 μm to 3.2 μm; and wherein the upstream resilient seal has an internal surface which forms a continuation of an internal surface of the reservoir to form a throat over the aperture plate; and wherein the throat is funnel-shaped and has an area in the plane of the aperture plate of at least 18 mm2.

23. The nebulizer as claimed in claim 1, wherein the upstream resilient seal is configured so that when under axial compression it forms an opening with an internal surface which is tapered inwardly in a flow direction to form a funnel shape at a throat over the aperture plate; and wherein the throat has an area in the plane of the aperture plate of at least 20 mm2 and which is at least twice the active area of the aperture plate.

24. A nebulizer, comprising:
- a housing;
- a liquid supply reservoir formed by the housing;
- an aerosol outlet formed by the housing; and
- an aerosol generator mounted within the housing and comprising:
  - a vibratable aperture plate;
  - an annular support supporting the aperture plate;
  - a vibration generator disposed downstream of the vibratable aperture plate and the annular support; and
  - a power conductor configured to transfer power to the vibration generator, wherein the power conductor includes at least one spring terminal extending from downstream of the vibration generator to upstream of the vibration generator and contacting an underside of the annular support.

25. A nebulizer, comprising:

a housing;

a liquid supply reservoir formed by the housing;

an aerosol outlet formed by the housing; and an aerosol generator mounted within the housing and comprising:

a vibratable aperture plate;

an annular support supporting the aperture plate;

a vibration generator disposed downstream of the vibratable aperture plate and the annular support; and a power conductor configured to transfer power to the vibration generator, wherein the power conductor includes a first spring pin engaging an upstream-facing surface of the annular support and a second spring pin engaging an upstream-facing surface of the vibration generator, and wherein the second spring pin extends through an aperture of the annular support without conductively contacting the annular support.

* * * * *